(12) United States Patent
Kaforey et al.

(10) Patent No.: US 12,721,771 B2
(45) Date of Patent: Sep. 1, 2026

(54) HEATED PATIENT POSITIONING DEVICE FOR SURGICAL PROCEDURES

(71) Applicant: Xodus Medical, Inc., New Kensington, PA (US)

(72) Inventors: Craig Kaforey, Allison Park, PA (US); Mark Kaforey, Murrysville, PA (US)

(73) Assignee: Xodus Medical, Inc., New Kensington, PA (US)

( * ) Notice: Subject to any disclaimer, the term of this patent is extended or adjusted under 35 U.S.C. 154(b) by 0 days.

(21) Appl. No.: 19/463,959

(22) Filed: Jan. 29, 2026

(65) Prior Publication Data

US 2026/0224423 A1 Aug. 6, 2026

Related U.S. Application Data

(60) Provisional application No. 63/752,322, filed on Jan. 31, 2025.

(51) Int. Cl.
*A61G 13/12* (2006.01)
*A61F 7/00* (2006.01)
(Continued)

(52) U.S. Cl.
CPC ............ *A61G 13/126* (2013.01); *A61F 7/007* (2013.01); *A61F 7/08* (2013.01); *B32B 3/085* (2013.01); *B32B 5/024* (2013.01); *B32B 5/026* (2013.01); *B32B 5/18* (2013.01); *B32B 5/245* (2013.01); *A61F 2007/0071* (2013.01); *A61F 2007/0086* (2013.01); *A61F 2007/0096* (2013.01); *A61F 2007/0098* (2013.01); *A61G 2203/46* (2013.01); *A61G 2210/90* (2013.01);
(Continued)

(58) Field of Classification Search
CPC .... A61F 7/007; A61F 7/08; A61F 2007/0071; A61F 2007/0086; A61F 2007/0096; A61F 2007/0098; A61G 13/126; A61G 2203/30; A61G 2203/46; A61G 2210/90
See application file for complete search history.

(56) References Cited

U.S. PATENT DOCUMENTS

| | | | |
|---|---|---|---|
| 513,813 | A | 1/1894 | Munro et al. |
| 2,764,150 | A | 9/1956 | Ettinger et al. |

(Continued)

FOREIGN PATENT DOCUMENTS

| | | | |
|---|---|---|---|
| CN | 110177402 | A | 8/2019 |
| WO | 2001095841 | A2 | 12/2001 |

(Continued)

*Primary Examiner* — Bradford C. Blaise
(74) *Attorney, Agent, or Firm* — The Webb Law Firm

(57) ABSTRACT

A heated patient support device for positioning a patient on an operating table during a surgical procedure includes a foam body having a substantially flat first surface configured to be in contact with the patient, an opposing substantially flat second surface configured to contact the operating table for holding the patient support device in place against the operating table, and a peripheral edge extending therebetween. The patient support device also includes at least one heating element at least partially enclosed within the foam body. The at least one heating element includes a cloth sheet and a graphene layer on a surface of the cloth sheet configured to generate heat when electric current is applied to the graphene layer.

19 Claims, 17 Drawing Sheets

(51) Int. Cl.

| | |
|---|---|
| ***A61F 7/08*** | (2006.01) |
| ***B32B 3/08*** | (2006.01) |
| ***B32B 5/02*** | (2006.01) |
| ***B32B 5/18*** | (2006.01) |
| ***B32B 5/24*** | (2006.01) |

(52) U.S. Cl.

CPC ... *B32B 2250/40* (2013.01); *B32B 2266/0278* (2013.01); *B32B 2307/202* (2013.01); *B32B 2307/51* (2013.01); *B32B 2307/7163* (2013.01); *B32B 2307/744* (2013.01); *B32B 2535/00* (2013.01)

(56) References Cited

U.S. PATENT DOCUMENTS

| | | | |
|---|---|---|---|
| 2,835,902 A | 5/1958 | Bernice | |
| 3,227,440 A | 1/1966 | Scott | |
| 3,512,190 A | 5/1970 | Buff | |
| 3,670,725 A | 6/1972 | Gaylord, Jr. | |
| 3,780,387 A | 12/1973 | Propst | |
| 4,135,504 A | 1/1979 | Spann | |
| 4,717,611 A | 1/1988 | Petrella et al. | |
| 4,840,362 A | 6/1989 | Bremer et al. | |
| 4,989,849 A | 2/1991 | Zupancic et al. | |
| 5,015,037 A | 5/1991 | Giblin et al. | |
| 5,054,142 A | 10/1991 | Owens | |
| 5,306,231 A | 4/1994 | Cullum et al. | |
| 5,324,911 A | 6/1994 | Cranston et al. | |
| 5,346,278 A | 9/1994 | Dehondt | |
| 5,362,302 A | 11/1994 | Jensen et al. | |
| 5,402,544 A | 4/1995 | Crawford et al. | |
| 5,448,790 A | 9/1995 | Saro et al. | |
| 5,628,078 A | 5/1997 | Pennington et al. | |
| 5,661,860 A | 9/1997 | Heitz | |
| 5,669,094 A | 9/1997 | Swanson | |
| 5,778,887 A * | 7/1998 | Curtiss | A61G 7/07 128/845 |
| 5,784,734 A | 7/1998 | Scott et al. | |
| 5,802,640 A | 9/1998 | Ferrand et al. | |
| 5,893,183 A | 4/1999 | Bechtold, Jr. | |
| 6,237,172 B1 | 5/2001 | Morgan, Sr. | |
| 6,401,283 B2 | 6/2002 | Thomas et al. | |
| 6,516,483 B1 | 2/2003 | VanSteenburg | |
| 6,541,094 B1 | 4/2003 | Landvik et al. | |
| 6,568,010 B1 | 5/2003 | Ames | |
| 6,620,488 B2 | 9/2003 | Oguri et al. | |
| 6,622,727 B2 | 9/2003 | Perry | |
| 6,653,363 B1 | 11/2003 | Tursi, Jr. et al. | |
| 6,754,923 B2 | 6/2004 | Borders et al. | |
| 6,772,764 B2 | 8/2004 | Chapman | |
| 6,817,363 B2 | 11/2004 | Biondo et al. | |
| 6,866,915 B2 | 3/2005 | Landvik | |
| 6,880,189 B2 | 4/2005 | Welling et al. | |
| 6,904,631 B2 | 6/2005 | Vrzalik et al. | |
| 7,076,822 B2 | 7/2006 | Pearce | |
| 7,176,419 B2 | 2/2007 | Ellis et al. | |
| 7,189,214 B1 | 3/2007 | Saunders | |
| 7,196,289 B2 | 3/2007 | Ellis et al. | |
| 7,240,384 B2 | 7/2007 | Dudonis | |
| 7,441,293 B1 | 10/2008 | Singer et al. | |
| 7,552,493 B2 | 6/2009 | McNulty | |
| 7,555,794 B2 | 7/2009 | Zelnik et al. | |
| 7,603,730 B2 | 10/2009 | Zelnik | |
| 7,731,283 B2 | 6/2010 | Leeds | |
| 7,757,318 B2 | 7/2010 | Poulos et al. | |
| 7,849,540 B2 | 12/2010 | Hill | |
| 7,971,298 B2 | 7/2011 | Kobub et al. | |
| 8,011,045 B2 | 9/2011 | Skripps | |
| 8,464,720 B1 | 6/2013 | Pigazzi et al. | |
| 8,510,885 B2 | 8/2013 | Dennis et al. | |
| 8,555,890 B2 | 10/2013 | Hiebert | |
| 9,161,876 B2 | 10/2015 | Pigazzi et al. | |
| 9,693,891 B2 | 7/2017 | MacIntyre-Ellis et al. | |
| 9,782,287 B2 | 10/2017 | Pigazzi et al. | |
| 11,266,525 B2 | 3/2022 | Kaforey et al. | |
| 2002/0096311 A1 | 7/2002 | Kushnir et al. | |
| 2004/0044091 A1 | 3/2004 | Niederoest et al. | |
| 2004/0149711 A1* | 8/2004 | Wyatt | A61F 7/007 219/217 |
| 2004/0153132 A1* | 8/2004 | Cobb | A61F 7/0085 607/104 |
| 2004/0256381 A1 | 12/2004 | Haas | |
| 2005/0210595 A1 | 9/2005 | Di Stasio et al. | |
| 2006/0016016 A1 | 1/2006 | Hornbach | |
| 2006/0020311 A1 | 1/2006 | Ellis et al. | |
| 2006/0112490 A1 | 6/2006 | Chausse | |
| 2006/0248650 A1 | 11/2006 | Skripps | |
| 2008/0010751 A1 | 1/2008 | Kemper et al. | |
| 2008/0173629 A1* | 7/2008 | Deibel | H05B 3/342 219/494 |
| 2008/0178390 A1 | 7/2008 | DuDonis | |
| 2008/0255538 A1 | 10/2008 | Ellis | |
| 2008/0255641 A1* | 10/2008 | Ellis | A61F 7/02 607/96 |
| 2009/0025150 A1 | 1/2009 | Smalling et al. | |
| 2009/0275808 A1 | 11/2009 | DiMaio et al. | |
| 2010/0212087 A1 | 8/2010 | Leib et al. | |
| 2010/0275377 A1 | 11/2010 | West | |
| 2010/0281617 A1 | 11/2010 | Brun | |
| 2011/0092890 A1 | 4/2011 | Stryker et al. | |
| 2011/0263950 A1 | 10/2011 | Larson et al. | |
| 2012/0022620 A1* | 1/2012 | Khodak | A61G 11/00 5/601 |
| 2013/0073012 A1 | 3/2013 | Ellis | |
| 2013/0174854 A1 | 7/2013 | Pigazzi et al. | |
| 2013/0289150 A1 | 10/2013 | Hager et al. | |
| 2013/0327339 A1 | 12/2013 | Chua | |
| 2015/0238021 A1 | 8/2015 | Wassermann | |
| 2015/0241147 A1* | 8/2015 | Brooks | F28F 21/02 165/185 |
| 2015/0289817 A1 | 10/2015 | Augustine et al. | |
| 2016/0299543 A1* | 10/2016 | Brooks | H05B 3/145 |
| 2017/0209305 A1* | 7/2017 | Kaforey | A61G 13/10 |
| 2017/0258630 A1 | 9/2017 | Pedro et al. | |
| 2018/0193185 A1* | 7/2018 | Thomas | A61F 7/007 |
| 2020/0179160 A1 | 6/2020 | Noah | |
| 2021/0136879 A1 | 5/2021 | Jeon | |
| 2022/0047315 A1* | 2/2022 | Baker | A61F 7/00 |
| 2023/0156869 A1* | 5/2023 | Rurs | H05B 3/145 219/112 |
| 2023/0340719 A1* | 10/2023 | Yang | B32B 5/00 |
| 2024/0156661 A1 | 5/2024 | Kaforey | |
| 2025/0126683 A1* | 4/2025 | Howe | C09D 11/50 |
| 2025/0374379 A1* | 12/2025 | Du | A47G 9/0215 |

FOREIGN PATENT DOCUMENTS

| | | |
|---|---|---|
| WO | 2004093758 A1 | 11/2004 |
| WO | 2008110922 A2 | 9/2008 |
| WO | 2008110923 A2 | 9/2008 |
| WO | 2010086740 A1 | 8/2010 |
| WO | 2018200743 A1 | 11/2018 |

* cited by examiner

HEATED PATIENT POSITIONING DEVICE FOR SURGICAL PROCEDURES

CROSS REFERENCE TO RELATED APPLICATION

The present application claims the benefit of U.S. Provisional Patent Application No. 63/752,322, filed Jan. 31, 2025, the disclosure of which is hereby incorporated by reference in its entirety.

BACKGROUND

Field of the Invention

The present disclosure relates generally to patient positioning and support devices for cushioning and positioning a patient during a surgical procedure and, in particular, to a heated patient support device comprising a heating element, as well as to a controller and power supply for supplying electric current to the heating element.

Description of Related Art

Maintaining patient positioning during a surgical procedure is important for patient safety. Patient positioning devices, such as mats, pads, mattresses, cushions, and pillows, are used for holding a patient in a desired position during a surgical procedure. For example, elongated foam pads, such as pads formed from egg-crate foam, can be placed between a patient's torso and an operating table for comfort. Also, foam pillows of different shapes can be used to hold arms, shoulders, legs, and other body parts in desired positions during a surgical procedure. In some cases, the patient positioning devices can include integral straps, cables, or ties for securing the devices in place on the operating table at desired positions. In other examples, medical tape, twist ties, or temporary adhesives can be used for tying or otherwise securing the positioning devices in place.

Maintaining patient normothermia (e.g., normal body temperature) is also important for assuring patient safety during a surgical procedure. Many devices and methods are available for this purpose. Most simply, a caregiver can cover the patient with a blanket. However, a blanket may not be effective to warm a patient, as it depends solely on the patient's body heat, which may not be sufficient to maintain normothermia. Devices and methods are also available that provide heat from source(s) external to a patient. An example of a device including an artificial or external heating element is the Bair Hugger™ manufactured by 3M Corporation, which blows heated air into an inflatable, forced air warming blanket with an external blower.

However, there is a need in the art for improved patient positioning and warming systems and devices that effectively secure the patient to the operating table in a desired position for an entirety of a surgical procedure, while maintaining patient normothermia throughout the surgical procedure. The devices, systems, and electronic controllers of the present disclosure are configured to address these issues.

SUMMARY

According to an aspect of the disclosure, a heated patient support device for positioning a patient on an operating table during a surgical procedure includes a foam body having a substantially flat first surface configured to be in contact with the patient, an opposing substantially flat second surface configured to contact the operating table for holding the patient support device in place against the operating table, and a peripheral edge extending therebetween. The patient support device also includes at least one heating element at least partially enclosed within the foam body. The at least one heating element includes a cloth sheet and a graphene layer on a surface of the cloth sheet configured to generate heat when electric current is applied to the graphene layer.

According to another aspect of the disclosure, a patient warming system includes the patient support device, as previously described, which further includes at least one temperature sensor for measuring a temperature of the patient support device proximate to the heating element. The warming system also includes at least one controller configured supply the electric current to the at least one heating element causing the at least one heating element to produce heat to warm the patient support device.

According to another aspect of the disclosure, a method of assembly for a heated patient support device includes a step of assembling at least one heating element having a cloth sheet and a graphene layer over an inwardly facing surface of the cloth sheet. The at least one heating element is configured to generate heat when an electric current is applied to the graphene layer. The method also includes steps of: removing a lower removable cover sheet from a lower surface of the at least one heating element exposing a lower adhesive layer; attaching the at least one heating element to a lower foam block such that the lower adhesive layer adheres the at least one heating element to the lower foam block; removing a removable upper cover sheet from an upper surface of the at least one heating element exposing an upper adhesive layer; and attaching the at least one heating element to the upper foam block such that the upper adhesive layer adheres the at least one heating element to the upper foam block, thereby enclosing the at least one heating element between the upper foam block and the lower foam block forming the heated patient support device.

According to another aspect of the disclosure, a controller configured supply electric current to at least one heating element of a heated patient support device causing the at least one heating element to generate heat, the at least one controller includes: a power supply; a cable interface configured to receive signals from one or more temperature sensors of the patient support device over a cable extending from the patient support device and to provide the electric current from the power supply to the at least one heating element of the patient support device over the cable; a display screen configured to display a selected setpoint temperature for the patient support device; and at least one processor. The at least one processor is configured to cause the power supply to provide the electric current to the at least one heating element over the cable based on a comparison between a temperature of the patient support device determined from the received signals and the selected setpoint temperature.

Non-limiting illustrative examples of embodiments of the present disclosure will now be described in the following numbered clauses.

Clause 1: A heated patient support device for positioning a patient on an operating table during a surgical procedure, the patient support device comprising: a foam body comprising a substantially flat first surface configured to be in contact with the patient, an opposing substantially flat second surface configured to contact the operating table for holding the patient support device in place against the operating table, and a peripheral edge extending therebetween; and at least one heating element at least partially enclosed within the foam body, the at least one heating element comprising a cloth sheet and a graphene layer on a surface of the cloth sheet configured to generate heat when electric current is applied to the graphene layer.

Clause 2: The support device of clause 1, wherein the foam body comprises viscoelastic foam.

Clause 3: The support device of clause 1 or clause 2, wherein the foam body comprises an upper foam block comprising the first surface and a lower foam block comprising the second surface, and wherein the at least one heating element is positioned between the upper foam block and the lower foam block.

Clause 4: The support device of clause 3, wherein the upper foam block and the lower foam block comprise a same type of biodegradable and viscoelastic foam material.

Clause 5: The support device of clause 3 or clause 4, wherein the upper foam block is at least 50% thicker than the lower foam block.

Clause 6: The support device of any of clauses 1-5, wherein portion(s) of the foam body configured to contact the operating table have a coefficient of friction sufficient to restrict the foam body from sliding over the operating table when the operating table is moved to an angle between 10 degrees and 45 degrees.

Clause 7: The support device of any of clauses 1-6, wherein portion(s) of the foam body configured to be in contact with the patient are configured to form depressions within the foam body due to body weight of the patient, the depressions preventing the patient from sliding over the first surface of the foam body.

Clause 8: The support device of any of clauses 1-7, wherein the at least one heating element comprises a pair of conductive bus bars extending along opposing longitudinal edges of the patient support device and in electrical contact with the graphene film on the sheet.

Clause 9: The support device of any of clauses 1-8, wherein the at least one heating element further comprises at least one temperature sensor for measuring a temperature of the patient support device proximate to the heating element.

Clause 10: The support device of any of clauses 1-9, wherein the at least one heating element further comprises a plurality of temperature sensors for measuring a temperature of the patient support device positioned over the graphene film for measuring temperature proximate to the graphene film.

Clause 11: The support device of any of clauses 1-10, wherein the cloth sheet comprises a woven or knitted cloth sheet.

Clause 12: The support device of any of clauses 1-11, wherein the cloth sheet comprises a non-stretch polyester knitted fabric.

Clause 13: The support device of any of clauses 1-12, wherein the at least one heating element comprises first and second copper film segments extending along opposing sides of the foam body, and wherein the graphene layer comprises a plurality of graphene segments extending between the first copper film segment and the second copper film segment.

Clause 14: The support device of clause 13, wherein the first and second copper film segments are substantially parallel to longitudinal sides of the patient support device and the plurality of graphene segments are substantially parallel to latitudinal sides of the support device.

Clause 15: The support device of clause 13 or clause 14, wherein the plurality of graphene segments are about 5 mm to 15 mm wide and spaced apart from adjacent graphene segments by at least about 5 mm.

Clause 16: The support device of any of clauses 1-15, wherein the at least one heating element comprises: a first insulation portion comprising the cloth sheet and adhesive over an outwardly facing surface of the cloth sheet; the graphene layer on an inwardly facing surface of the cloth sheet; a second insulation portion comprising another cloth sheet and adhesive over an outwardly facing surface of the another cloth sheet; a copper film between the first insulation portion and the second insulation portion; and a silver adhesive layer between the graphene layer and the copper film that adheres the copper film to the graphene layer and to the cloth sheet.

Clause 17: The support device of any of clauses 1-16, comprising a single-use disposable patient support device, and wherein the foam body is biodegradable.

Clause 18: The support device of any of clauses 1-17, wherein the heating element has an IPXX rating for solid particle protection of from 1 to 6 and for liquid ingress protection of from 1 to 9.

Clause 19: The support device of any of clauses 1-18, wherein the heating element has an IPXX rating for solid particle protection of 3 or greater and for liquid ingress protection of 6 or greater.

Clause 20: The support device of any of clauses 1-20, wherein the heating element has an IPXX rating of IP58.

Clause 21: A patient warming system, comprising: the patient support device of any of clauses 1-20, wherein the at least one heating element further comprises at least one temperature sensor for measuring a temperature of the patient support device proximate to the heating element, and at least one controller configured supply the electric current to the at least one heating element causing the at least one heating element to produce heat to warm the patient support device.

Clause 22: The patient warming system of clause 21, wherein the at least one controller is configured to receive and process temperature information from the at least one temperature senor; determine a temperature of the patient support device based on the received and processed information; compare the determined temperature to a setpoint temperature value; and cease applying the electric current to the at least one heating element when the determined temperature is equal to or exceeds the setpoint value.

Clause 23: The patient warming system of clause 22, wherein the controller comprises a user interface configured to permit a user to manually enter the setpoint temperature value.

Clause 24: The patient warming system of clause 22 or clause 23, wherein, in response to comparing the determined temperature to the setpoint temperature value, the at least one controller is configured to reduce the electric current applied to the at least one heating element linearly until the determined temperature is within two degrees of the setpoint temperature value and then to adjust the electric current according to a proportional-integral-derivative (PID) algorithm when the measured temperature is within two degrees of the setpoint temperature value.

Clause 25: The patient warming system of any of clauses 22-24, wherein the setpoint temperature value is a value input by a user of from about 36° C. to about 40° C.

Clause 26: The patient warming system of any of clauses 22-25, wherein the at least one controller comprises user input buttons allowing a user to modify the setpoint temperature value between a minimum setpoint temperature (e.g., 36° C.) and a maximum setpoint temperature (e.g., 40° C.).

Clause 27: The patient warming system of any of clauses 21-26, wherein the at least one heating element of the patient support device comprises multiple temperature sensors, and wherein the at least one controller is configured to cease applying the electric current to the at least one heating element when a maximum temperature measured by any of the multiple temperature sensors is above a predetermined threshold temperature value.

Clause 28: The patient warming system of any of clauses 21-27, wherein the at least one heating element of the patient support device comprises multiple temperature sensors, and wherein the at least one controller is configured to cease applying electric current to the at least one heating element when temperatures detected by the multiple temperature sensors vary by more than about 5° C.

Clause 29: The patient warming system of any of clauses 21-28, wherein the at least one controller is configured to initiate a controller self-test at start-up, the self-test comprising a battery check, a cable check, and a patient support device check.

Clause 30: The patient warming system of clause 29, wherein the at least one controller is configured to perform the battery check, which comprises comparison of voltage of the battery measured by the at least one controller to a threshold minimum voltage.

Clause 31: The patient warming system of clause 29 or clause 30, wherein the controller is configured to perform the cable check and generate a cable check alert when the cable check identifies the following conditions: all temperature sensors of the at least one heating element have an open circuit with a measured resistance substantially exceeding expected values; and a dedicated overtemperature monitoring circuit of the patient support device indicates an error.

Clause 32: The patient warming system of any of clauses 29-31, wherein the at least one controller is configured to provide a notification to replace the patient support device when the patient support device check determines that one or more of the following conditions have occurred: electric current of the patient support device measured by the at least one controller is outside of a predetermined acceptable range; a dedicated overtemperature circuit error occurs; any of the temperature sensors measure a resistance substantially greater than an expected value; or any of the temperature sensors measure resistance values indicating a temperature substantially greater than an acceptable maximum temperature.

Clause 33: The patient warming system of any of clauses 29-32, wherein the at least one controller is configured to enter an operation safe mode when: output voltage of a power supply of the at least one controller is outside of a predetermined range; output electric current to the patient support device is outside of a predetermined range; any of the temperature sensors measure a resistance substantially greater than an expected value; any of the temperature sensors measure resistance indicating a temperature substantially greater than a predetermined maximum permitted temperature; or temperatures detected by multiple temperature sensors differ by more than about 5° C.

Clause 34: A method of assembly for a heated patient support device, comprising: assembling at least one heating element comprising a cloth sheet and a graphene layer over an inwardly facing surface of the cloth sheet, the at least one heating element being configured to generate heat when an electric current is applied to the graphene layer; removing a lower removable cover sheet from a lower surface of the at least one heating element exposing a lower adhesive layer; attaching the at least one heating element to a lower foam block such that the lower adhesive layer adheres the at least one heating element to the lower foam block; removing a removable upper cover sheet from an upper surface of the at least one heating element exposing an upper adhesive layer; and attaching the at least one heating element to the upper foam block such that the upper adhesive layer adheres the at least one heating element to the upper foam block, thereby enclosing the at least one heating element between the upper foam block and the lower foam block forming the heated patient support device.

Clause 35: The method of clause 34, wherein the lower foam block and the upper foam block comprise viscoelastic foam.

Clause 36: The method of clause 34 or clause 35, wherein the upper foam block and the lower foam block comprise a same type of biodegradable and viscoelastic foam material.

Clause 37: The method of clause 36, wherein the upper foam block is at least 50% thicker than the lower foam block.

Clause 38: The method of any of clauses 34-37, wherein the sheet comprises a woven or knitted cloth sheet.

Clause 39: The method of any of clauses 34-38, wherein the cloth sheet comprises a non-stretch polyester knitted fabric.

Clause 40: The method of any of clauses 34-39, wherein assembling the at least one heating element comprises: applying the graphene layer to the cloth sheet; forming a pair of conductive bus bars on opposing longitudinal edges of the at least one heating element and contacting the graphene layer; connecting a plurality of temperature sensors to the cloth sheet at different positions on the cloth sheet; adhering or laminating another cloth sheet over the cloth sheet thereby enclosing the graphene layer and pair of conductive bus bars between the cloth sheets; applying adhesive to outwardly facing surfaces of the cloth sheets, thereby forming the upper adhesive layer and the lower adhesive layer; and attaching the upper and lower removable cover sheets to the upper and lower adhesive layers, thereby forming the at least one heating element.

Clause 41: The method of clause 40, wherein applying the graphene layer to the cloth sheet comprises applying a plurality of spaced apart, linear graphene segments on to the cloth sheet.

Clause 42: The method of clause 41, wherein the pair of conduct bus bars are formed over the plurality of graphene segments such that the plurality of graphene segments extend between the pair of conductive bus bars.

Clause 43: The method of clause 42, wherein the plurality of graphene segments are about 5 mm to 15 mm wide and spaced apart from adjacent graphene film segments by at least about 5 mm.

Clause 44: A controller configured supply electric current to at least one heating element of a heated patient support device causing the at least one heating element to generate heat, the at least one controller comprising: a power supply; a cable interface configured to receive signals from one or more temperature sensors of the patient support device over a cable extending from the patient support device and to provide the electric current from the power supply to the at least one heating element of the patient support device over the cable; a display screen configured to display a selected setpoint temperature for the patient support device; and at least one processor configured to cause the power supply to provide the electric current to the at least one heating element over the cable based on a comparison between a temperature of the patient support device determined from the received signals and the selected setpoint temperature.

Clause 45: The controller of clause 44, further comprising a housing enclosing the cable interface, the display screen, and the at least one processor, and at least one clip attached to a rear surface of the housing configured to secure the housing to a pole.

Clause 46: The controller of clause 45, wherein the at least one clip comprises articulating arms configured to grasp the pole for holding the controller in place on the pole.

Clause 47: The controller of clause 45 or clause 46, wherein a bottom surface of the housing is substantially flat so that the controller can be positioned on a flat surface in an upright orientation.

Clause 48: The controller of any of clauses 44-47, wherein the at least one processor is configured to receive and process temperature information from the one or more temperature sensors; determine a temperature of the patient support device based on the received and processed information; compare the determined temperature to the setpoint temperature value; and cease applying the electric current to the at least one heating element when the determined temperature is equal to or exceeds the setpoint value.

Clause 49: The controller of clause 48, further comprising a user interface configured to permit a user to manually enter the setpoint temperature value.

Clause 50: The controller of clause 49, wherein the user interface comprises a positive temperature button that when pressed by the user increases the setpoint temperature and a negative temperature button that when pressed decreases the setpoint temperature.

Clause 51: The controller of any of clauses 48-50, wherein, in response to the comparison between the determined temperature to a setpoint temperature value, the at least one controller is configured to reduce the electric current applied to the at least one heating element linearly until the determined temperature is within two degrees of the setpoint temperature value and then to adjust the electric current according to a proportional-integral-derivative (PID) algorithm when the measured temperature is within two degrees of the setpoint temperature value.

Clause 52: The controller of any of clauses 44-51, wherein the setpoint temperature value is between about 36° C. to about 40° C.

Clause 53: The controller of any of clauses 44-52, wherein the at least one heating element of the patient support device comprises multiple temperature sensors, and wherein the at least one processor is configured to cause the power supply to cease applying the electric current to the at least one heating element when a maximum temperature measured by any of the multiple temperature sensors is above a predetermined maximum permitted temperature value.

Clause 54: The controller of any of clauses 44-53, wherein the at least one heating element of the patient support device comprises multiple temperature sensors, and wherein the at least one processor of the controller is configured to cause the power supply to cease applying electric current to the at least one heating element when temperatures detected by the multiple temperature sensors vary by more than about 5° C.

Clause 55: The controller of any of clauses 44-54, wherein the at least one processor is configured to initiate a controller self-test at start-up, the self-test comprising a battery check, a cable check, and a patient support device check.

Clause 56: The controller of clause 55, further comprising a backup battery, wherein the at least one processor is configured to perform the battery check, which comprises comparison of voltage of the backup battery measured by a voltage sensor to a threshold minimum voltage.

Clause 57: The controller of clause 55 or clause 56, wherein the at least one processor is configured to perform the cable check and generate a cable check alert when the cable check identifies the following conditions: all temperature sensors of the at least one heating element of the patient support device have an open circuit with a measured resistance substantially exceeding expected values; and a dedicated overtemperature monitoring circuit of the patient support device indicates an error.

Clause 58: The controller of any of clauses 55-57, wherein the at least one processor is configured to provide a notification to replace the patient support device when the patient support device check determines that one or more of the following conditions have occurred: electric current of the patient support device measured by a current sensor of the controller is outside of a predetermined acceptable range; a dedicated overtemperature monitoring circuit of the patient support device indicates an error; any of the temperature sensors of the patient support device measure a resistance substantially greater than an expected value; or any of the temperature sensors of the patient support device detect resistance signals indicating that temperature of the patient support device is substantially greater than a maximum permitted temperature.

Clause 59: The controller of any of clauses 55-58, wherein the at least one processor is configured to cause the controller to enter an operation safe mode when: output voltage of the power supply of the controller is outside of a predetermined range; output electric current to the patient support device is outside of a predetermined range; any of the temperature sensors of the patient support device detect a resistance substantially greater than an expected value; any of the temperature sensors of the patient support device detect resistance indicating a temperature substantially greater than a predetermined maximum permitted temperature; or temperatures detected by multiple temperature sensors differ by more than about 5° C.

BRIEF DESCRIPTION OF THE DRAWINGS

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limit of the invention.

DETAILED DESCRIPTION

Figure 1A:
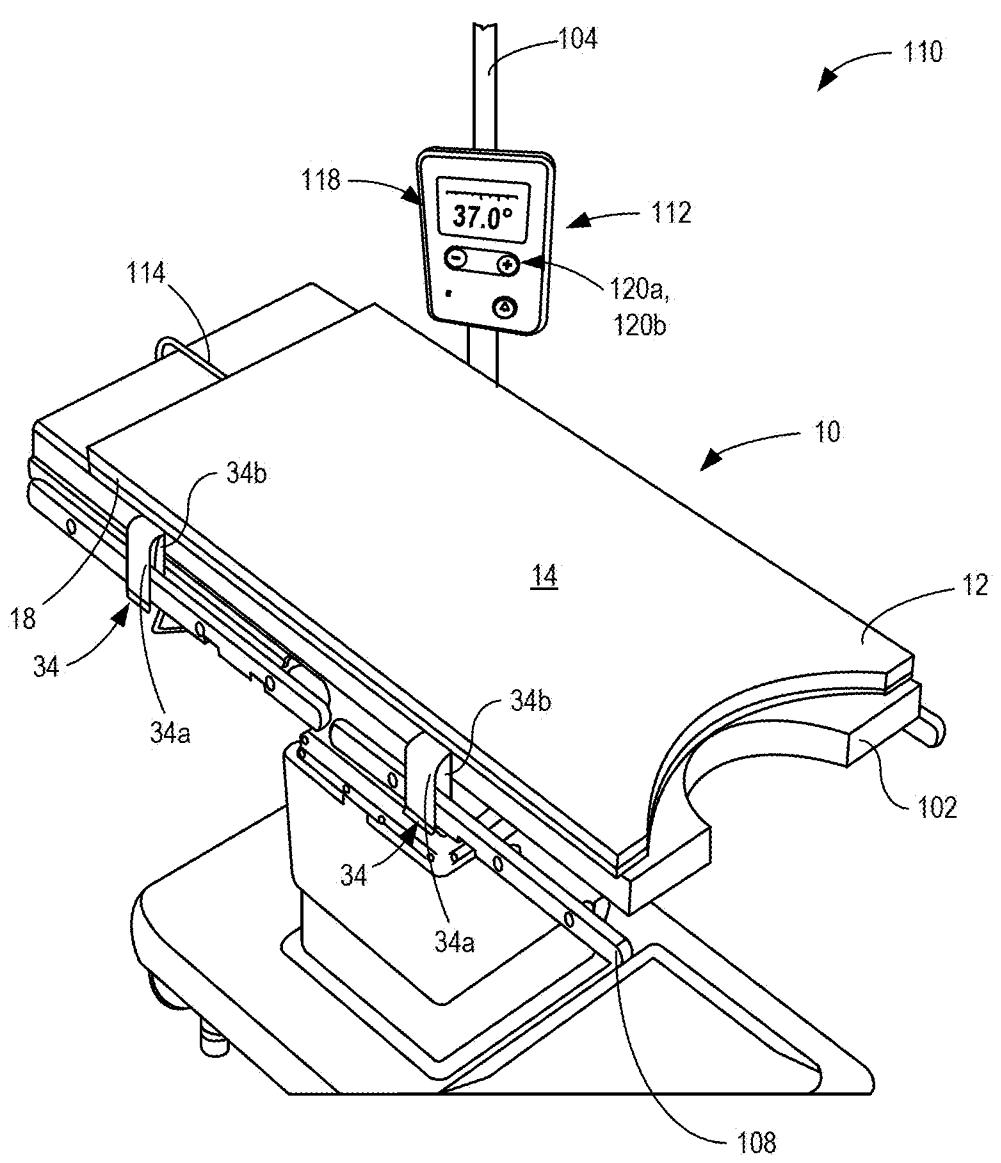
FIG. 1A is a perspective view of a patient warming system comprising a patient support device, according to an example of the present disclosure.

As used herein, the singular form of "a", "an", and "the" include plural referents unless the context clearly dictates otherwise. For the purposes of this specification, unless otherwise indicated, all numbers expressing quantities of ingredients, reaction conditions, dimensions, physical characteristics, and so forth used in the specification and claims are to be understood as being modified in all instances by the term "about."

As used herein, the terms "right", "left", "top", and derivatives thereof shall relate to the invention as it is oriented in the drawing figures. However, it is to be understood that the invention can assume various alternative orientations and, accordingly, such terms are not to be considered as limiting. Also, it is to be understood that the invention can assume various alternative variations and stage sequences, except where expressly specified to the contrary. It is also to be understood that the specific devices and processes illustrated in the attached drawings, and described in the following specification, are examples. Hence, specific dimensions and other physical characteristics related to the embodiments disclosed herein are not to be considered as limiting.

Figure 1B:
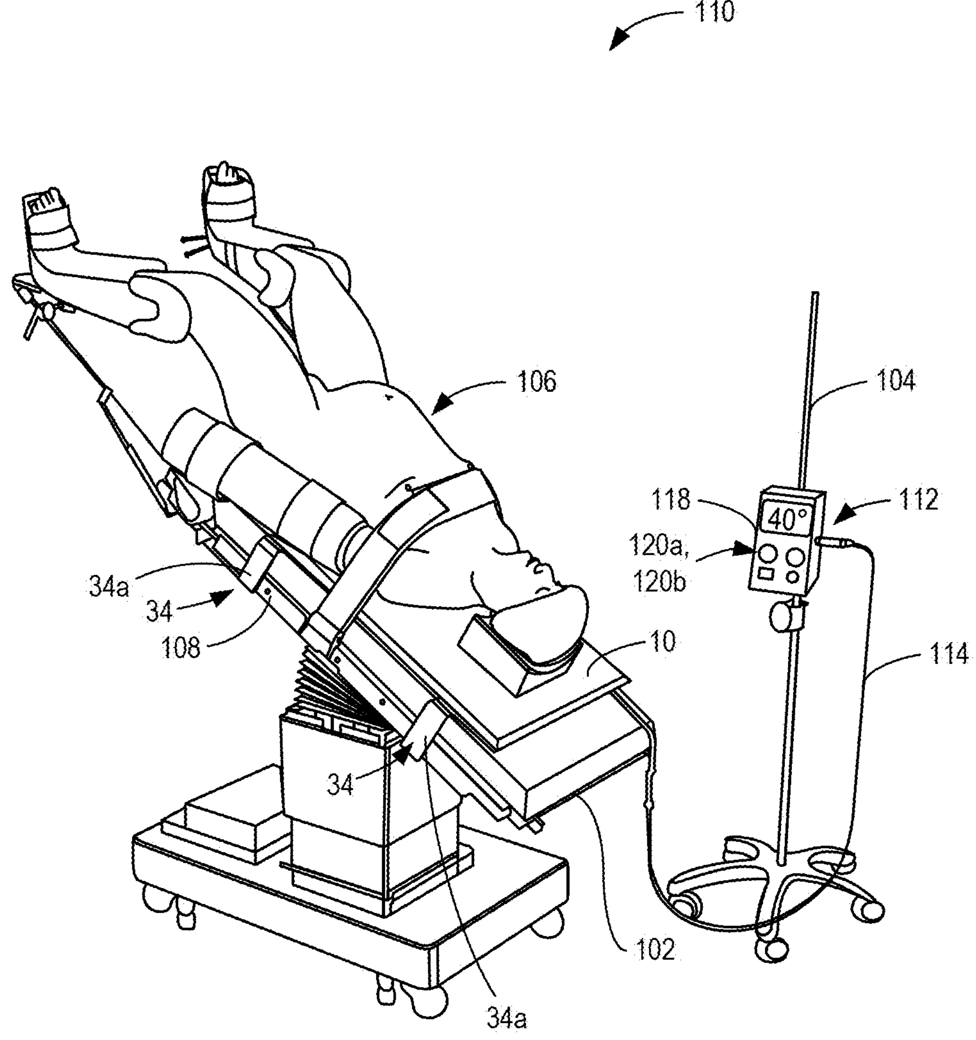
FIG. 1B is another perspective view of the patient warming system showing a patient being supported by a patient support device of FIG. 1A.

With reference to FIGS. 1A and 1B, the present disclosure is directed to a patient warming system 110 comprising a patient support device 10, cushion, or pad comprising and/or enclosing a heating element 20 (shown in FIGS. 2B and 2C) and a controller 112. The controller 112 is configured to apply electric current to the heating element 20 in a safe and controllable manner sufficient to maintain the patient support device 10 at a desired temperature (referred to herein as the setpoint temperature) and without exceeding a maximum permitted temperature. FIG. 1A shows the patient support device 10 on an operating table 102 and the controller 112 secured to a pole 104 or elongated support, such as an IV pole, positioned near the operating table 102. FIG. 1B is a drawing showing a patient 106 resting on and secured to the patient support device 10 for positioning and warming the patient 106 during the surgical procedure.

In examples, the patient support device 10 or pad is a disposable medical device configured to be placed on the operating table 102 during the surgical procedure and to be discarded after completion of a single surgical procedure. In examples, the patient support device 10 can also be placed on an examination table or hospital bed, for example, over or on top of a cushion or mattress of the table or bed. Alternatively or in addition, the patient support device 10 can be positioned on other objects and furniture of a medical facility, such as on other types of stretchers, beds, tables, or chairs. In other examples, the patient support device 10 can be positioned on the floor or any other flat surface at the hospital or medical facility for cushioning and warming the patient before, during, or after a medical procedure.

Because the patient support device 10 is intended for single-use, the patient support device 10 does not need to be cleaned, sterilized, or otherwise prepared for reuse by another patient. Instead, the patient support device 10 can be discarded after each procedure. Also, the patient support device 10 does not need to be covered or otherwise isolated from the patient 106 with, for example, a cover sheet or barrier. While the patient support device 10 is a disposable single-use device, the controller 112 can be a reusable electric device which can be detachably connected to the patient support device 10 with a cable 114, such as a pigtail cable or another suitable connector. After completion of the surgical procedure, the cable 114 extending from the patient support device 10 to the controller 112 can be detached from the controller 112 and, when ready for the next surgical procedure, a new patient support device 10 can be connected to the controller 112 for heating the new patient support device 10.

In examples, the patient support device 10 is configured to position the patient on the operating table 102 during the surgical procedure and to maintain patient positioning throughout different types of surgical procedures. In examples, the surgical procedure can include one or more of gynecological procedures, colorectal procedures, urological procedures, laparoscopic procedures, or robotic procedures. In a particular example, as shown in FIG. 1B, the patient support device 10 can be used to support a patient 106 in the Trendelenburg or the reverse Trendelenburg position, in which the operating table 102 positioned at an angle of from about 10 degrees to about 45 degrees, or preferably from about 15 degrees to about 30 degrees relative to horizontal. When activated, the heating element 20 of the patient support device 10 is configured to warm the patient support device 10 to a temperature near to or slightly above normal body temperature. For example, the heating element 20 can be configured to warm the patient support device 10 to a temperature of between 36° C. and 40° C.

Figure 2A:
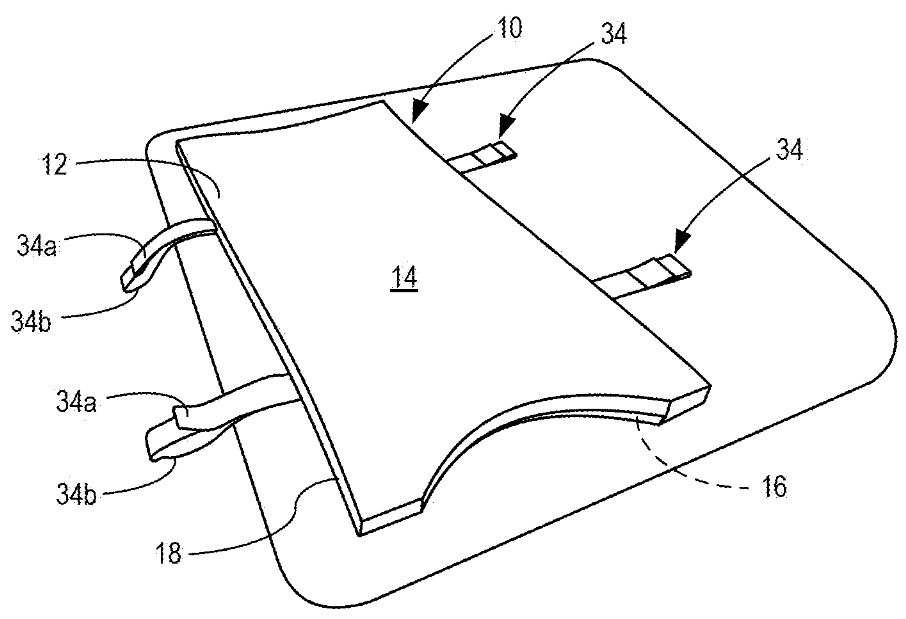
FIG. 2A is a perspective view of a patient support device, according to an example of the present disclosure.
Figure 2B:
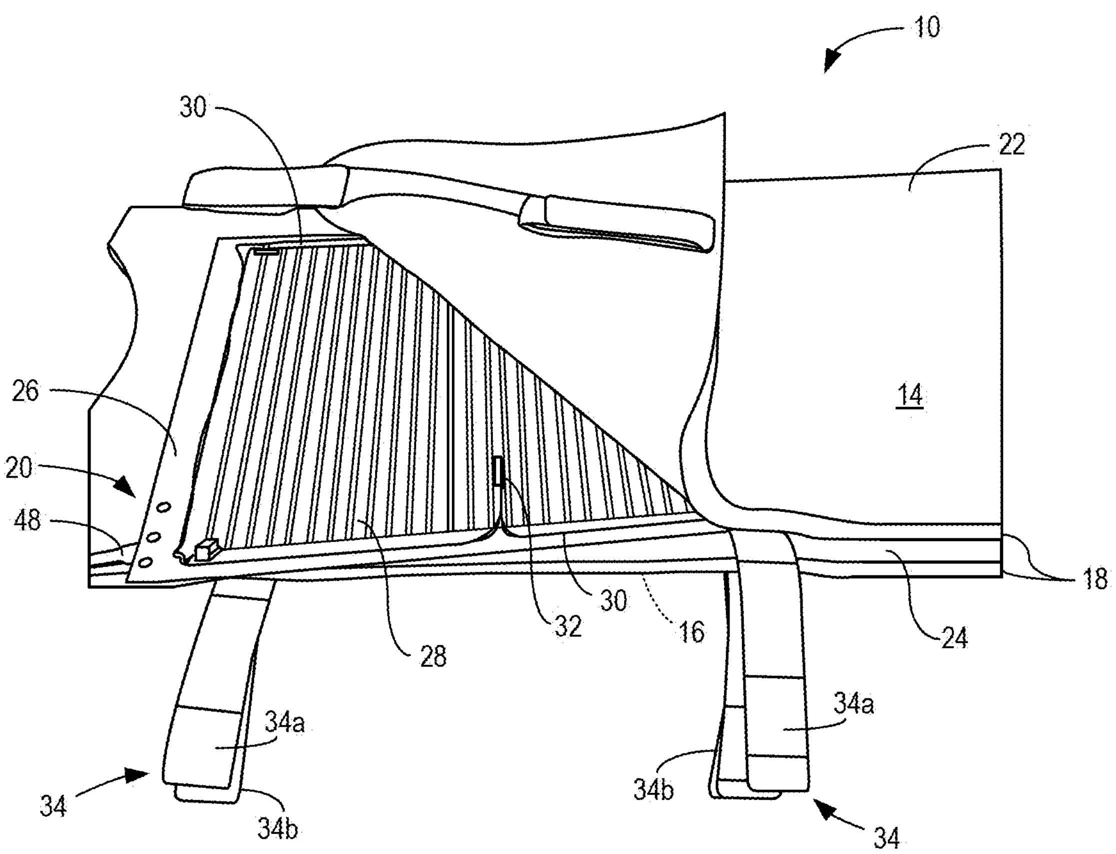
FIG. 2B is a perspective view showing a heating element between foam blocks of the patient support device of FIG. 2A.
Figure 2C:
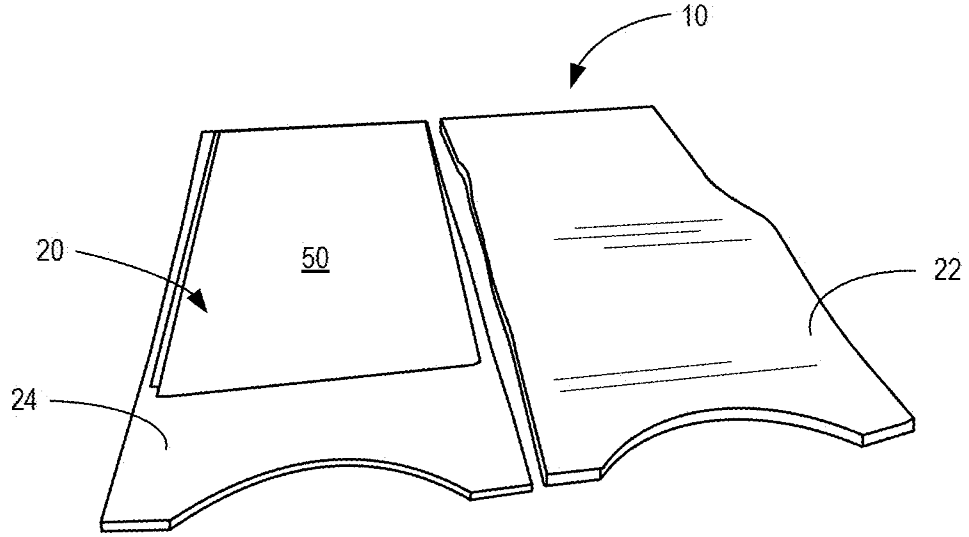
FIG. 2C is another perspective view of the patient support device of FIG. 2A, with an upper foam block separated from a lower foam block.

As shown in FIGS. 2A-2C, the patient support device 10 can comprise a foam body 12 with a lower surface 16 configured to contact the operating table 102. The lower surface 16 of the foam body 12 can have a coefficient of friction sufficient to restrict the foam body 12 from sliding over the surface of the operating table 102 when the operating table 102 is angled in the Trendelenburg position. Also, portion(s) of the foam body 12 of the patient support device 10 that are configured to be in contact with the patient 106 can form depressions within the foam body 12 due to body weight of the patient 106. The depressions can prevent the patient 106 from sliding over an upper surface 14 of the foam body 12, thereby maintaining patient 106 at a desired position on the patient support device 10 during the surgical procedure.

Figure 1C:
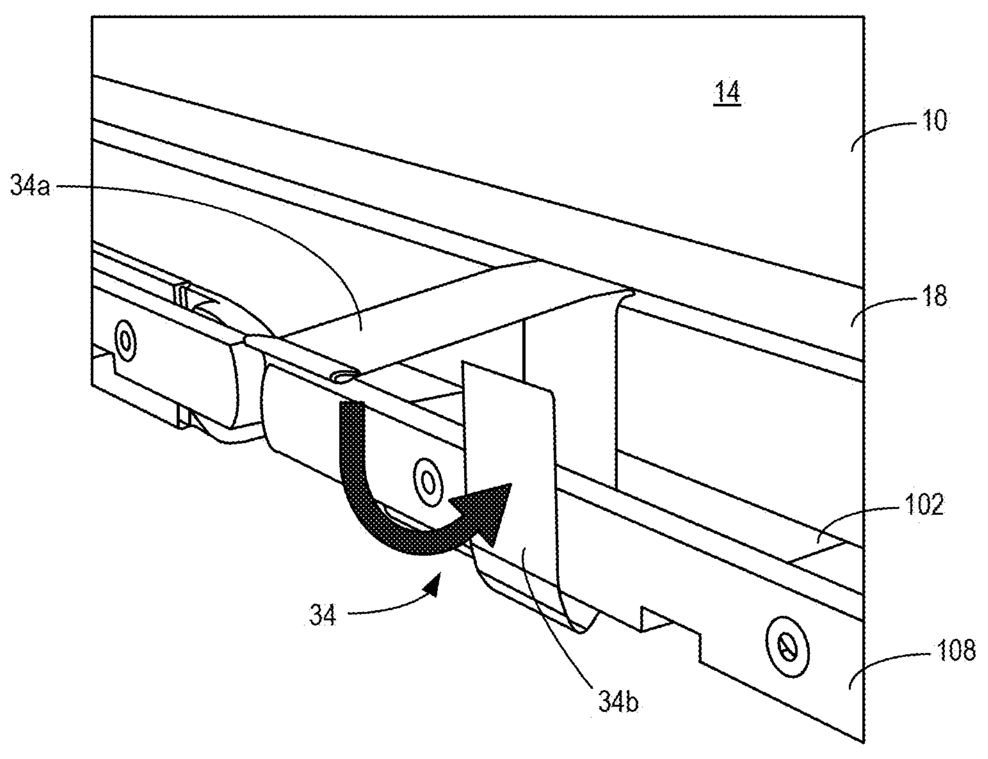
FIG. 1C is a drawing showing straps of the patient support device of FIG. 1A being attached to an operating table.

In examples, the patient support device 10 can also include straps 34 (shown in FIGS. 1A-2B) configured to be secured to portions of an operating table 102, such as to rails 108, sides, edges, or posts of the operating table 102, for helping to secure the patient support device 10 to the operating table 102 in a desired position. In some examples, the straps 34 can comprise a hook and loop fabric fastener (e.g., Velcro®) for attaching the straps 34 to the table or bed. Alternatively or in addition, the straps 34 can include ties, buckles, fasteners, or other connectors, known in the art, for attaching the straps 34 to portions of the operating table 102 or bed. In some examples, the straps 34 can include an upper strap 34*a* and a lower strap 34*b* configured to be attached to one another. For example, as shown in FIG. 1C, the lower strap 34*b* can be wrapped around the rails 108 of the bed 102 or table and then secured to the upper strap 34*a* by a fastener (e.g., a fabric hook and loop fastener), thereby securing the patient support device 10 to the operating table 102 or bed.

Figure 1D:
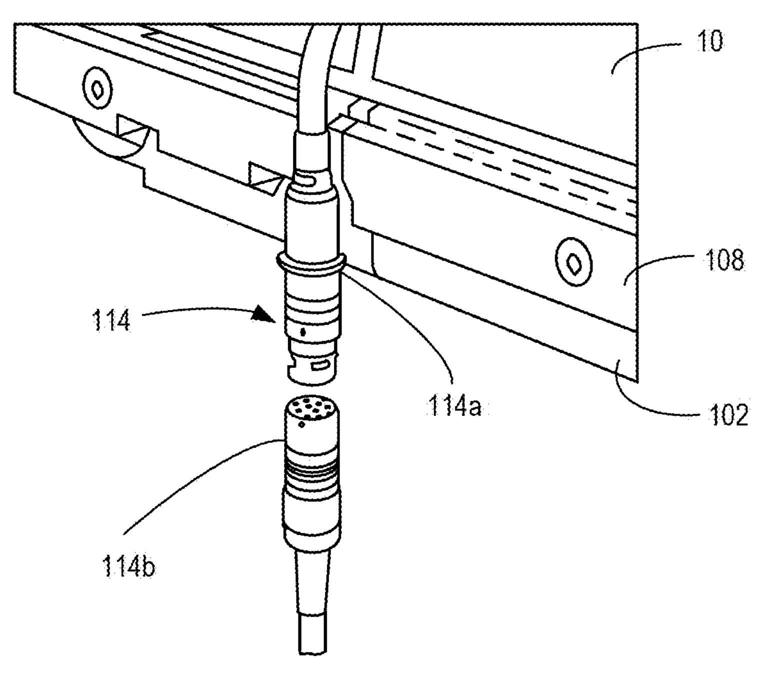
FIG. 1D is a drawing showing a cable of the patient support device of FIG. 1A.

In examples, the patient support device 10 further comprises the cable 114 extending from the patient support device 10 to the controller 112. In some examples, a single cable 114 can extend from the patient support device 10 and can include a plug or connector configured to be connected to a cable port of the controller 112. Alternatively, as shown in FIG. 1D, the patient support device 10 can comprise a short cable segment 114*a* extending from the patient support device 10. In that case, a second cable segment 114*b* can be connected between the end of the cable segment 114*a* and the cable port of the controller 112 for providing the electrical connection between the controller 112 and patient support device 10. In examples, the cable segments 114*a*, 114*b* can comprise pigtail connectors 116 (shown in FIG. 1D) or similar connectors for ensuring that there is a robust and secure electrical connection between cables of the patient support device 10 and the controller 112. However, as described previously, the cable segments 114*a*, 114*b* should be detachable from one another so that the patient support device 10 can be disconnected from the controller 112. In that case, the patient support device 10 can be detached and discarded and the controller 112 can be reused with a different patient support device 10.

Patient Support Device

FIGS. 2A-2C are drawings showing external and internal features and components of the patient support device 10. As shown in FIGS. 2A-2C, the patient support device 10 is a rectangular or substantially rectangular (e.g., nearly rectangular with corners within about 10% of) 90° cushion or pad that is about as wide as the operating table and long enough to support the patient's torso or whole body. In examples, the patient support device 10 comprises the foam body 12, which can comprise an upper foam block 22 and a lower foam block 24 (shown in FIGS. 2B and 2C). When the upper block 22 and the lower block 24 are joined together, the foam body 12 can comprise the flat or substantially flat (e.g., within about 10° of flat) first or upper surface 14 configured to be in contact with the patient 106, the opposing flat or substantially flat (e.g., within about 10° of flat) second or lower surface 16, and a peripheral edge 18 extending therebetween.

In some examples, the foam body 12 can comprise a foam (e.g., an open or closed cell foam) pad with a length sufficient to extend from at least thighs of the patient 106 to at least shoulders of the patient 106 to support the patient's torso. For example, the foam body 12 can have a length L (shown in FIG. 3A) of about 60 cm to 200 cm (about 25 inches to about 80 inches), a width W (shown in FIG. 3A) of about 25 cm to 100 cm (about 10 inches to 40 inches), and a thickness of about 1 cm to about 8 cm (about 0.5 inch to about 3.0 inches). In examples, the foam body 12 is preferably about 4 cm (about 1.5 inches) thick. Alternatively, in some examples, the foam body 12 can be a full length pad (e.g., about 150 cm to about 200 cm or about 60 inches to about 80 inches in length) that extends the entire length of the operating table 102 and supports the patient's entire body.

In examples, the upper foam block 22 can be thicker than the lower foam block 24, such as about 25%, 50%, or 75% thicker than the lower foam block 24. For example, the upper foam block 22 can be about 2.5 cm (1 inch thick) in thickness and the lower foam block 24 can be about 1 cm to 2 cm (0.5 inch to about 0.75 inch) in thickness.

As previously described, the foam body 12 and/or foam blocks 22, 24 can be formed from a viscoelastic foam material, often referred to as "memory foam." The viscoelastic foam material can be a high-viscosity foam which limits movement or sliding of the patient 106 on the foam body 12 and of the foam body 12 on the surface of the operating table 102. More particularly, the surface of the foam body 12 may have a high coefficient of static friction, stickiness, or tackiness that is sufficient to provide good engagement with the patient 106 and with the surface of the operating table 102. As a result of such surface properties, the patient 106 may, in effect, stick to the patient support device 10, even when the operating table 102 and patient support device 10 are angled (e.g., at an angle for from 10 degrees to 45 degrees).

In some examples, the viscoelastic foam material comprises a viscoelastic polyurethane foam material with a glass transition temperature that is substantially less than a glass transition temperature for a conventional (non-viscoelastic foam). For example, the viscoelastic polyurethane foam can have a glass transition temperature of about or exceeding 0° C. or, for example, between about −10° C. and about 10° C. or between about −5° C. and about 5° C. By contrast, glass transition temperature for a conventional (non-viscoelastic foam) is about −50° C.

In some examples, the viscoelastic foam material of the foam body 12 or blocks 22, 24 can have one or more of the following mechanical properties: a ball rebound (ASTM D-3574) of less than 40%, or less than about 20%, or about 0.1% to about 20%, or about 1% to about 10%; a density (ASTM D-3574) of about 1 pcf to about 10 pcf, or about 2 pcf to about 8 pcf, or about 5 pcf to about 6.5 pcf (about 15 kilograms per cubic meter to about 150 kilograms per cubic meter, or about 35 kilograms per cubic meter to about 128 kilograms per cubic meter, or about 83 kilograms per cubic meter to about 103 kilograms per cubic meter); and/or an indentation force deflection (ASTM D-3574) of about 5 lbf (2.25 kg) to about 20 lbf (9 kg), or about 7 lbf (3.1 kg) to about 15 lbf (6.8 kg). The viscoelastic foam material of the foam body 12 or blocks 22, 24 can also have one or more of the following mechanical properties: a compression set (22 hrs. @ 70° C.), for a 25 percent compression, of less than 0.5 percent (ASTM D-3574); an air flow in the range of 0.3 to 1.0 cubic foot per minute (ASTM D-3574); a tensile strength of about 8 pounds per square inch to about 12 pounds per square inch; and/or a coefficient of static friction of about 0.2 to about 2.5. Examples of viscoelastic foam materials, which can be used with the patient support device 10 and patient warming systems 110 of the present disclosure, are described, for example, in: U.S. Pat. Nos. 8,464,720; 9,161,876; 9,782,287; and 11,266,525, which are incorporated herein by reference in their entireties.

In some examples, the viscoelastic foam material of the foam body 12 or blocks 22, 24 can be a polyurethane foam (e.g., a foam made by mixing polyhydroxy polyol with toluene di-isocyanate, polyester polyols, and/or polyether polyols). As previously described, the selected viscoelastic foam material can have a coefficient of friction of from about 0.2 to about 2.5 to ensure sufficient frictional engagement to the patient 106 and/or surface of the operating table 102. In some examples, the foam body 12 or blocks 22, 24 can be formed from the same viscoelastic foam material (e.g., from a viscoelastic foam material having the same glass transition temperature, density, porosity, coefficient of friction, chemical composition, or other features).

In other examples, the blocks 22, 24 can be formed from different viscoelastic foam materials, such as materials having a different glass transition temperature, porosity, absorbance, or density. For example, the viscoelastic foam material of the upper block 22 can be more absorbent (e.g., moisture wicking) than the viscoelastic foam material of the lower block 24 in order to quickly and easily absorb any liquids, which may collect on an outer surface of the upper block 22 and/or on other portions of the patient support device 10. The material of the upper block 22 can also be less dense than the material of the lower block 24 to provide good patient comfort. In particular, the upper block 22 may be formed from a less dense (e.g., soft or plush) material that deforms under weight of the patient 106 creating a depression for receiving a portion of the patient's torso. By contrast, the lower block 24 can be formed from a denser material, which substantially maintains its shape when the patient's weight is exerted against the patient support device 10. As such, the lower block 24 may not deform in order to maintain good contact with the surface of the operating table 102 to hold the patient support device 10 in place against the table 102.

In some examples, the upper block 22 can be formed from an open-cell viscoelastic foam, which is absorbent and easily deformable. By contrast, the lower block 24 can be formed from a closed cell foam that is non-absorbent and/or which does not substantially deform under weight of the patient.

Because the patient support device 10 is intended to be a single-use disposable medical device, in some examples, the foam blocks 22, 24 of the foam body 12 can comprise a biodegradable, viscoelastic foam material. An exemplary material, which can be used for this purpose, is described in U.S. Patent Appl. Pub. No. 2024/0156661, which is incorporated by reference herein in its entirety. Using a biodegradable material can be especially important for patient support devices 10, such as the devices disclosed herein, which are intended to be single-use and discardable products. When made using biodegradable materials, the foam body 12 and/or other components of the patient support device 10 can be safely disposed of through aerobic and anaerobic solid-waste-treatment plants. Alternatively or in addition, the foam body 12 and/or other components of the patient support device 10 can be discarded to a biologically active landfill, with appropriate conditions to encourage degradation of biodegradable materials. In some instances, the foam body 12 can be separated from the heating element 20 prior to disposal so that the biodegradable foam components can be provided to the biologically active landfill, while the non-biodegradable heating element can be disposed of in another manner.

As used herein, a "biodegradable" or "bioerodible" material of the foam body 12 can be a material that degrades either partially or completely through chemical reactions and/or by action of living organisms (e.g., microbes). For example, a biodegradable viscoelastic foam material can degrade into component parts (e.g., water, carbon dioxide, simple or complex carbohydrates, and biomass). Preferably, the biodegradable material degrades over a reasonable time period of days, weeks, or months. Non-limiting examples of chemical reactions for biodegradable materials, such as biodegradable polymers, can include, for example, acid/base reactions, hydrolysis reactions, oxidation, and enzymatic cleavage. The biodegradation rate of the viscoelastic foam material can be adjusted so that the material degrades over a useful time period.

In some examples, the biodegradable viscoelastic foam material disclosed herein can be a material that is fully biodegradable as defined by the ASTM D5511-18 standard, which describes anaerobic biodegradation of plastic materials under high-solids anaerobic-digestion conditions. For example, the foam body 12 can be configured to degrade by at least 70% within 30 days under testing conditions specified by ASTM D5511-18. Specifically, the percentage of biodegradability can be obtained by determining a percent of conversion of carbon from the test material (e.g., the foam body 12) to carbon in a gaseous phase ($CH_4$ and $CO_2$). The percentage of biodegradability does not include an amount of carbon from the test material (e.g., the foam body 12) that is converted to cell biomass and that is not, in turn, metabolized to $CO_2$ and $CH_4$. In other examples, the foam body 12 can be configured to degrade by at least 80%, 90%, or 95% within 30 days under the ASTM D5511-18 testing conditions. In other examples, the foam body 12 can be configured to degrade by at least 70%, within 10 days under the ASTM D5511-18 testing conditions.

The patient support device 10 further comprises the heating element 20 at least partially enclosed within the foam body 12, such as between the upper foam block 22 and the lower foam block 24. The heating element 20 comprises a sheet 26, which can be a woven or kitted cloth sheet, such as a sheet of a non-stretch polyester knitted fabric, and a graphene layer, such as a graphene film 28, over a surface of the sheet 26. The cloth sheet 26 is a generally flexible material that can bend or flex to accommodate the patient's body weight. In particular, the cloth sheet 26 is intended to bend or flex to accommodate the depressions in the upper foam block 22 formed when the patient is on the patient support device 10. Also, the material of the cloth sheet 26 is selected to avoid wrinkling, folding, or forming creases under the patient's body weight in order to enhance patient comfort compared to more rigid materials.

The graphene film 28 can be printed or otherwise deposited on an inwardly facing surface of the sheet 26 in a pattern selected to evenly distribute heat over patient contacting surface(s) or area(s) of the foam body 12. The outwardly facing surface of the sheet can be covered with adhesive 40 (shown in FIG. 3B) for adhering the outwardly facing surface of the sheet 26 to one of the blocks 22, 24 of the foam body 12. In examples, as shown in FIG. 3B, the heating element 20 can also include a second cloth sheet 42 positioned over the graphene film 28 with an inwardly facing surface of the second cloth sheet 42 facing the inwardly facing surface of the cloth sheet 26. The outwardly facing surface of the second cloth sheet 42 can be coated with the adhesive 40 for adhering the cloth sheet 42 to one of the foam blocks 22, 24 of the foam body 12. The cloth sheets 26, 42 can be laminated or adhered together forming an enclosed heating element 20 that is substantially impervious to ingress of solid particles (e.g., dust) and liquids.

The Ingress Protection (IP or IPXX) code classifies the degree of protection provided by mechanical casings and electrical enclosures against intrusion, dust, accidental contact, and water. The IPXX rating for an electrical enclosure is provided as a two-digit rating (i.e., IP58), with the first digit referring to solid particle protection (from 0 to 6) and the second digit referring to liquid ingress protection (from 0 to 9). The cloth sheets 26, 42 of the heating element 20 are configured to provide substantial protection from ingress of solid particles (e.g., dust) and liquids (e.g., water). In examples, the IPXX rating for the heating element 20 can range between 1 to 6 for solid particle protection and between 1 to 9 for liquid ingress protection. For example, the heating element 20 can have an IPXX rating of IP11, IP22, IP36, IP58, IP69, or other values within the acceptable ranges. More particularly, the IPXX rating for solid particle ingress of the heating element 20 can be greater than 3, greater than 4, or greater than 5. The IPXX rating for liquid ingress protection for the heating element 20 can be greater than 5, greater than 7, or greater than 8. In a preferred example, the IPXX rating for the heating element 20 is IP58.

The graphene film 28 is configured to receive electric current from a power supply of the controller 112 and has an electric resistance selected to generate heat when the electric current is applied thereto. In examples, the amount of graphene film 28 can be selected so that the patient support device 10 can be warmed to slightly above body temperature. Desirably, the graphene film 28 does not heat to a temperature substantially above normal body temperature to prevent discomfort or injury to the patient 106. For example, the graphene film 28 can be selected to heat to a maximum permitted temperature of, for example, 42° C.

Figure 3A:
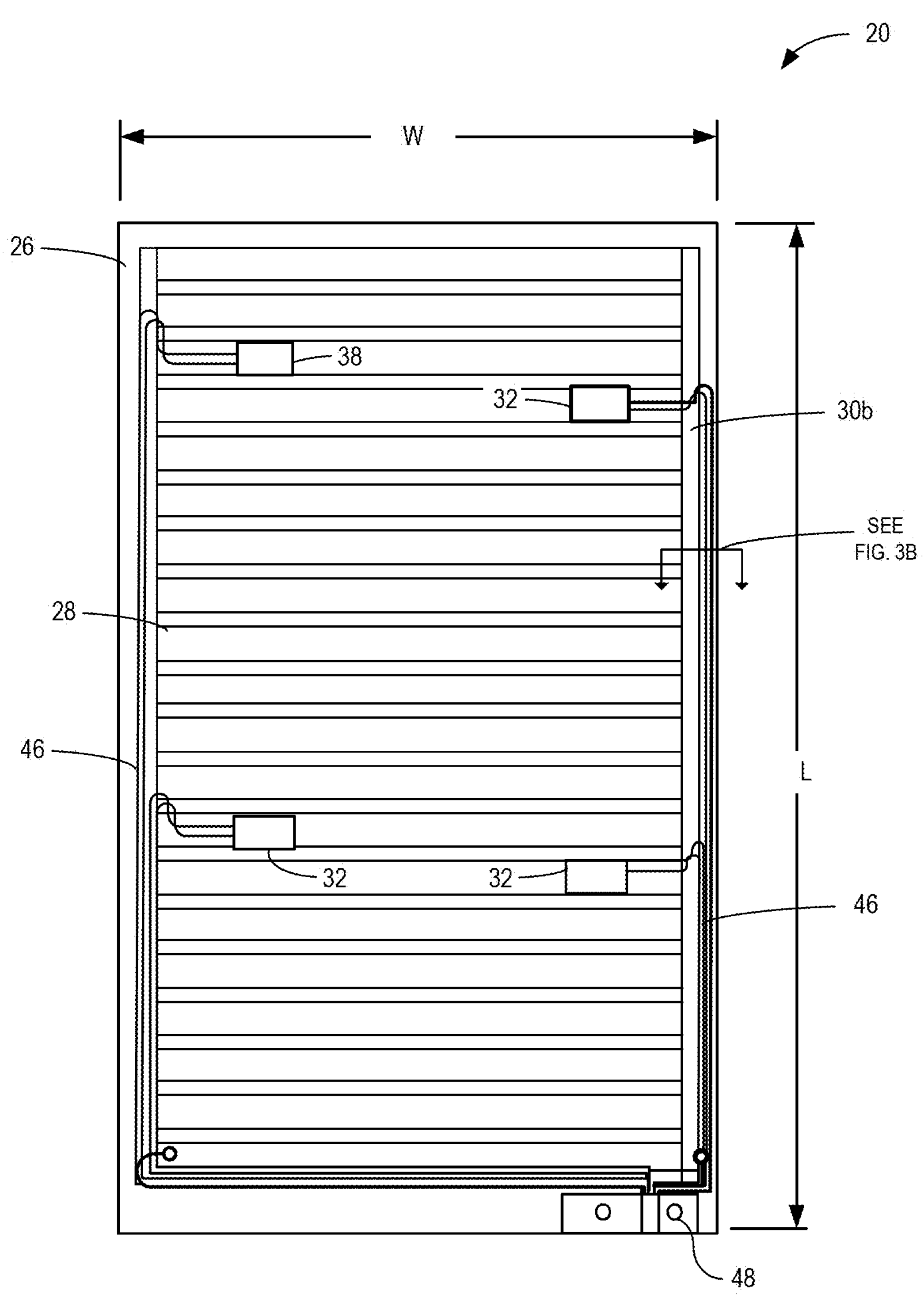
FIG. 3A is a schematic drawing of a top view of a heating element of a patient support device, according to an example of the present disclosure.
Figure 3B:
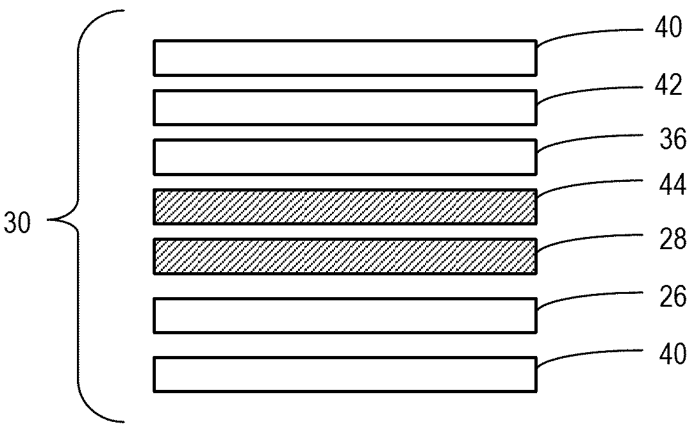
FIG. 3B is a cross sectional view of a portion of the heating element of FIG. 3A, taken along line 3B shown in FIG. 3A.

As shown in FIGS. 3A and 3B, the heating element 20 includes a pair of conductive bus bars 30*a*, 30*b* extending along opposing longitudinal edges of the patient support device 10 and in electrical contact with the graphene film 28 on the cloth sheet 26. In examples, the bus bars 30 can comprise copper film layers 36 (shown in FIG. 3B) deposited on the sheet 26 along the longitudinal edges of the sheet 26 and over portions of the graphene film 28. The bus bars 30*a*, 30*b* can be connected to the power source of the controller 112 by insulated wires 46 (e.g., insulated copper wires) or other sealed conductive connectors. As shown in FIG. 3A, the graphene film 28 is deposited on the sheet 26 as a series of spaced apart linear segments extending between a first bus bar 30*a* and a second bus bar 30*b* of the heating element 20. By way of example and as shown in FIG. 3A, a heating element 20 that is 77 cm long and 46 cm wide comprises twenty linear graphene segments. Each segment is about 5 mm to 15 mm wide. The segments are spaced apart by small gaps of about 5 mm. However, longer heating elements 20 may include additional segments and/or segments that are wider or spaced farther apart. By contrast, heating elements that are shorter than 77 cm may include fewer linear graphene segments and/or segments that are narrower or spaced closer together.

With continued reference to FIG. 3A, the heating element 20 can further comprise the one or multiple thermistors or temperature sensors 32, 38 for measuring a temperature of the patient support device 10 proximate to the heating element 20. As shown in FIG. 3A, the heating element 20 can comprise four temperature sensors 32, 38 at different positions on the graphene film 28 for detecting temperature proximate to the graphene film 28. In particular, as shown in FIG. 3A, the heating element 20 can comprise three temperature sensors 32 positioned over the graphene film 28 for measuring actual temperature of the heating element 20. In examples, the temperature sensors 32 can be configured to output a resistance signal which can be calibrated to temperature, with higher resistance representing lower detected temperature. As described in further detail herein, signals from the temperature sensors 32 can be used by the controller 112 to determine when to supply electric current to the heating element 20 so that the patient support device 10 remains at the setpoint temperature (e.g., a temperature of between 36° C. and 40° C.) selected by the user. The heating element 20 can also comprise an overtemperature sensor 38. The overtemperature sensor 38 can be a binary sensor configured to provide a signal to the controller 112 when a temperature of the patient support device 10 exceeds the maximum permitted temperature. Upon receiving the signal from the overtemperature sensor 38, the controller 112 can be configured to turn off the power supply and cease providing electric current to the patient support device 10. In some instances, the controller 112 can also be configured to provide an alert or alarm, such as a replace pad alert, when an overtemperature error is identified by the over temperature sensor 38.

FIG. 3B is a cross-sectional view of the bus bar portion 30 of the heating element 20 showing multiple layers of waterproof insulation (e.g., having an IPXX rating of 1-6 for solid particle protection and 1-9 for liquid ingress protection), adhesive, and conductive material that may be present in the heating element 20. As shown in FIG. 3B, the heating element 20 comprises insulation portions or layers formed from the cloth sheets 26, 42 with adhesive layers 40 disposed on outwardly facing surfaces of the cloth sheets 26, 42. As previously described, the graphene layer 28 is deposited on an inwardly facing surface of the cloth sheet 26 or, alternatively, on the inwardly facing surface of the other cloth sheet 42. The combination of the cloth sheets 26, 42 and adhesive 40 forms the waterproof and protective enclosure for the heating element 20 that prevents ingress of solid particles (e.g., dust) and liquid (e.g., water) to the bus bar portion 30 and other electrical components of the heating element 20.

As shown in FIG. 3B, the bus bar portion of the heating element 20 further comprises a copper film layer 36 that forms the bus bars 30*a*, 30*b* (shown in FIG. 3A). For example, as previously described, the copper film layers 36 or bus bars 30*a*, 30*b* extend along longitudinal edges of the heating element 20 and, as shown in FIG. 3B, can be over and in electrical connection with the graphene film 28. In examples, the heating element 20 can further comprise a conductive adhesive 44, such as a silver adhesive layer or paste, between the copper film layer 36 and the graphene film 28 for enhancing the electrical connection between the copper film layer 36 or bus bars 30 and the graphene film 28.

Assembly Method for a Patient Support Device

Figure 4A:
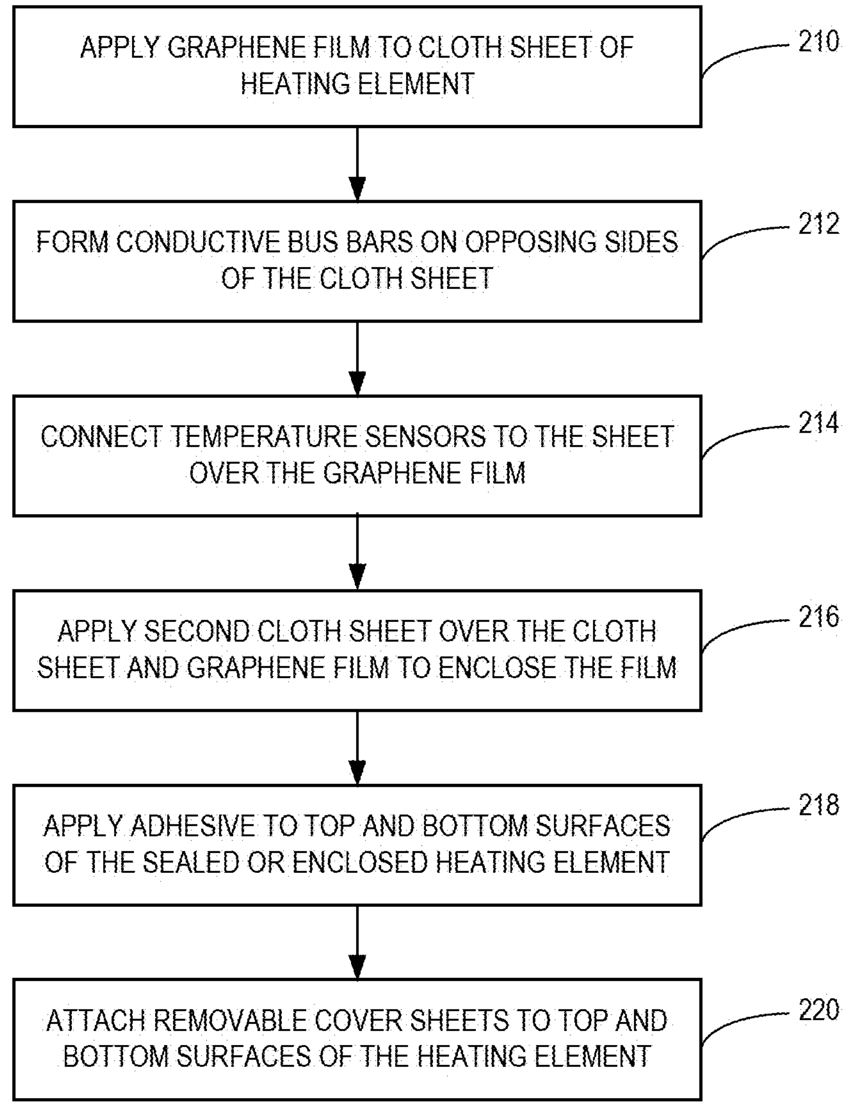
FIGS. 4A and 4B are flow charts showing methods of assembling a heating element and patient support device, according to examples of the present disclosure.
Figure 4B:
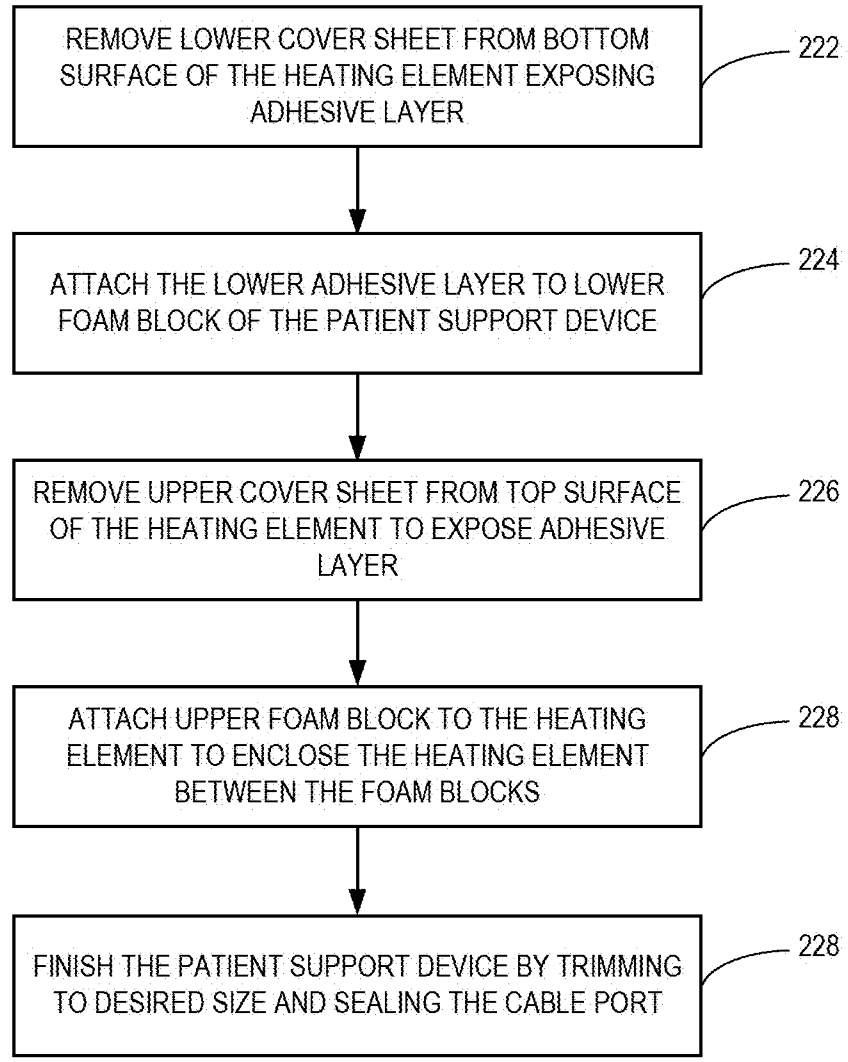

FIGS. 4A and 4B are flow charts showing steps of methods for assembling the heating element 20 and patient support device 10. In examples, the method for assembling the heating element 20 comprises an initial step 210 of applying the graphene film 28 to a sheet 26, such as to a cloth sheet (e.g., a sheet of non-stretch polyester knitted cloth). For example, the graphene film 28 can be printed to a surface of the sheet 26, deposited using a mask or template, or by another deposition technique or process known in the art. As previously described, the graphene film 28 can be deposited as spaced apart linear segments configured to extend between the bus bars 30 of the heating element 20.

At step 212, the method further comprises forming conductive bus bars 30 on opposing sides (e.g., opposing longitudinal edges) of the heating element 20 and in contact with the graphene film 28. In examples, forming the bus bars 30 can comprise applying the conductive adhesive 44 (e.g., a silver adhesive layer) over the graphene film 28 at intended locations for the bus bars 30. Next, the copper film layers 36 can be deposited on the conductive adhesive 44, such that the copper film layers 36 are electrically connected to the graphene film 28 through the conductive adhesive 44. Also, in examples, conductive segments such as copper wires 46 can be attached to portions of the copper film layers 36. The conductive segments or copper wires 46 can be connected to a cable or cable port 48 (shown in FIG. 3A), which is configured to receive or connect to the cable 114 extending from the controller 112 for providing electric current through the cable 114 and to the graphene film 28 through the electrical connectors 46 or copper wires and copper film layers 36.

The method next comprises a step 214 of connecting temperature sensors 32, 38 to the sheet 26 and over the graphene film 28 for monitoring temperature of the graphene film 28. In particular, as previously described, the three temperature sensors 32 for measuring the actual temperature of the graphene film 28 can be applied at different locations over the graphene film 28 as shown in FIG. 3A. The overtemperature sensor 38 for detecting when the graphene film 28 exceeds a maximum permitted temperature can also be positioned on the sheet 26 and over the graphene film 28 at a desired location. Wires extending from the temperature sensors 32, 38 can be positioned on the sheet 26 for providing an electrical connection between the temperature sensors 32, 38 and the cable port 48.

At step 216, the method for assembling the heating element 20 can further comprise attaching or adhering a second cloth sheet 42 to the cloth sheet 26, thereby enclosing the graphene film 28 and bus bars 30 together between inwardly facing surfaces of the cloth sheets 26, 42. As previously described, the cloth sheets 26, 42 form a waterproof and protective enclosure, such as an enclosure having an IPXX rating of 1-6 for solid particle protection and 1-9 for liquid ingress protection. The enclosure step 216 can be a lamination process in which adhesive (e.g., a thermoplastic adhesive) is applied to surfaces of the sheets 26, 42 and over the graphene film 28. In examples, the cloth sheets 26, 42 can also extend over or around the cable port 48 for ensuring that the electrical connection between the heating element 20 and cable port 48 is also sealed and waterproof.

At step 218, the method further comprises, after the heating element 20 is enclosed or laminated, applying adhesive to top and bottom surfaces of the sealed or enclosed heating element 20. At step 220, the method further comprises applying removable cover sheets 50 (shown in FIG. 2C) to the surfaces of the heating element 20, which can remain in place until a manufacturer is ready to assemble the patient support device 10.

FIG. 4B shows the method for assembling the patient support device 10 from the assembled heating element 20. As shown in FIG. 4B, the method for assembling the patient support device 10 comprises an initial step 222 of removing the lower removable cover sheet 50 from a lower surface of the heating element 20 exposing a lower adhesive layer. Once the lower adhesive layer is exposed, the method comprises a step 224 of attaching the lower adhesive layer to the lower foam block 24 of the foam body 12 by, for example, pressing the heating element 20 firmly against the lower foam block 24 so that the heating element 20 adheres to the lower foam block 24.

At step 226, the method further comprises removing the removable cover sheet 50 from an upper surface of the heating element 20 to expose the upper adhesive layer. With the upper adhesive layer exposed, the method further comprises, at step 228, attaching or adhering the upper foam block 22 to the heating element 20, thereby enclosing the heating element 20 between the upper foam block 22 and the lower foam block 24. At step 230, the method can further comprise finishing steps, such as cutting or trimming the patient support device 10 to a desired size. Finishing steps can also include applying waterproof sealant or adhesive around the cable port 48 and/or any electrical cables extending from the heating element 20. Finishing steps can also comprise attaching the straps 34 to the patient support device 10 and, for example, packing the patient support device 10 in suitable packaging material to prepare for shipping.

Patient Warming System

Figure 5A:
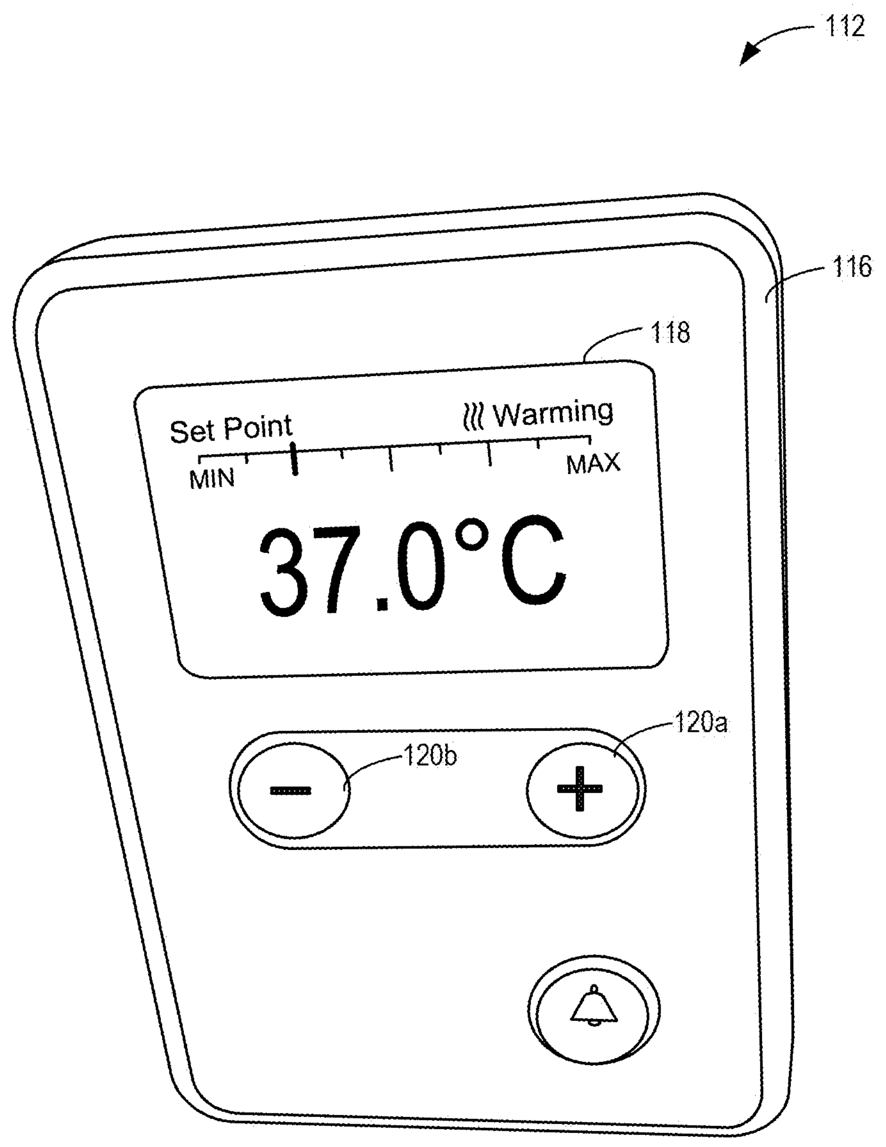
FIG. 5A is a front perspective view of a controller of a patient warming system, according to an example of the present disclosure.
Figure 5B:
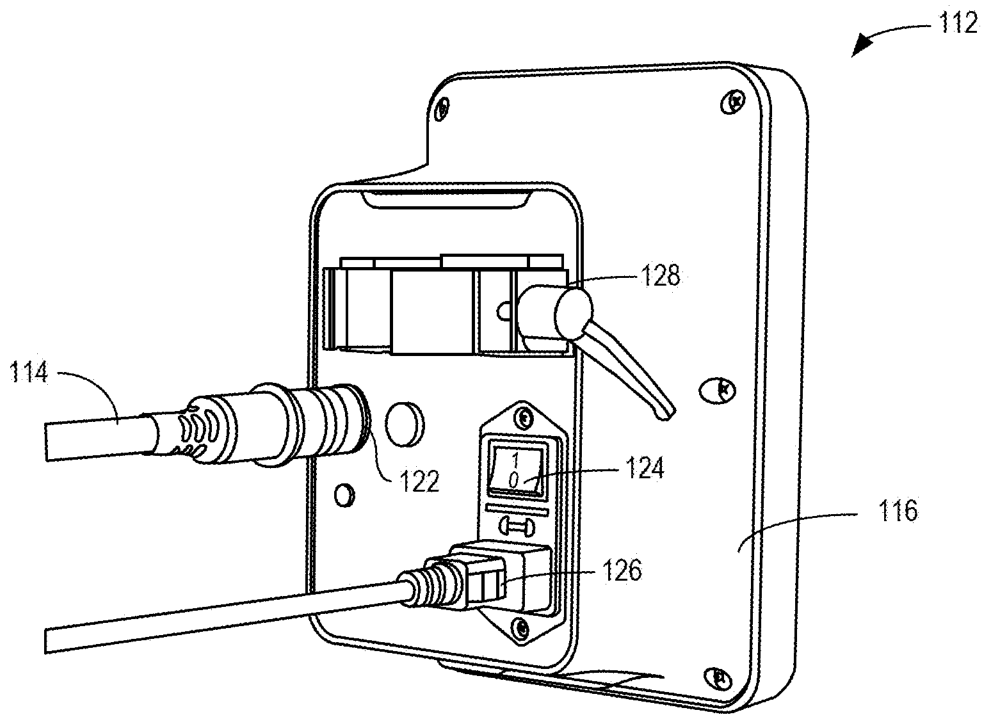
FIG. 5B is a rear perspective view of the controller of FIG. 5A.
Figure 5C:
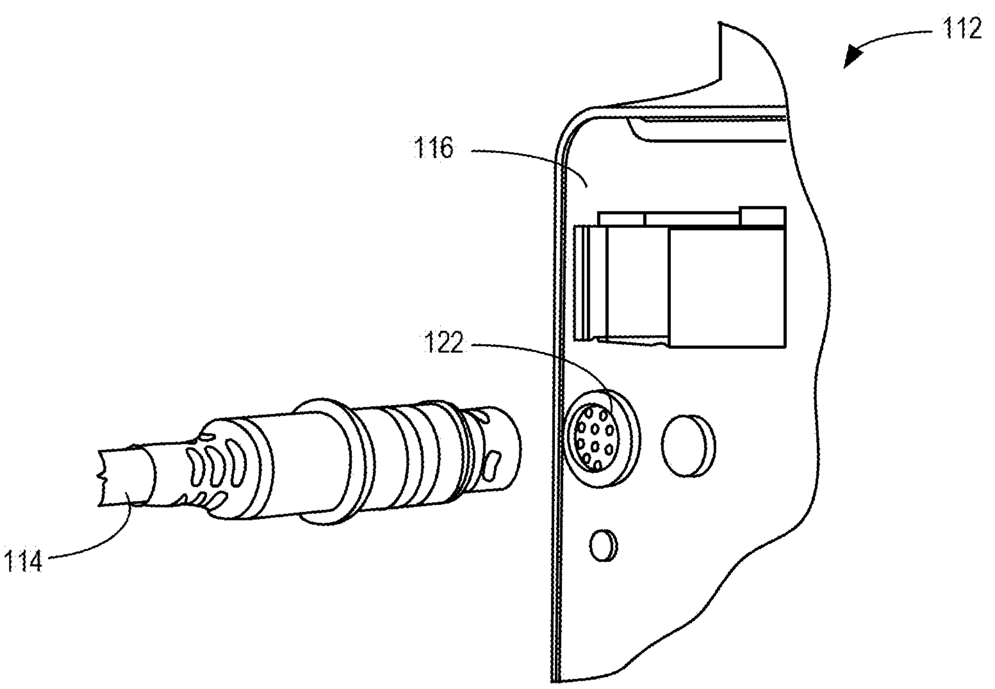
FIG. 5C is another rear perspective view of the controller of FIG. 5A.
Figure 5D:
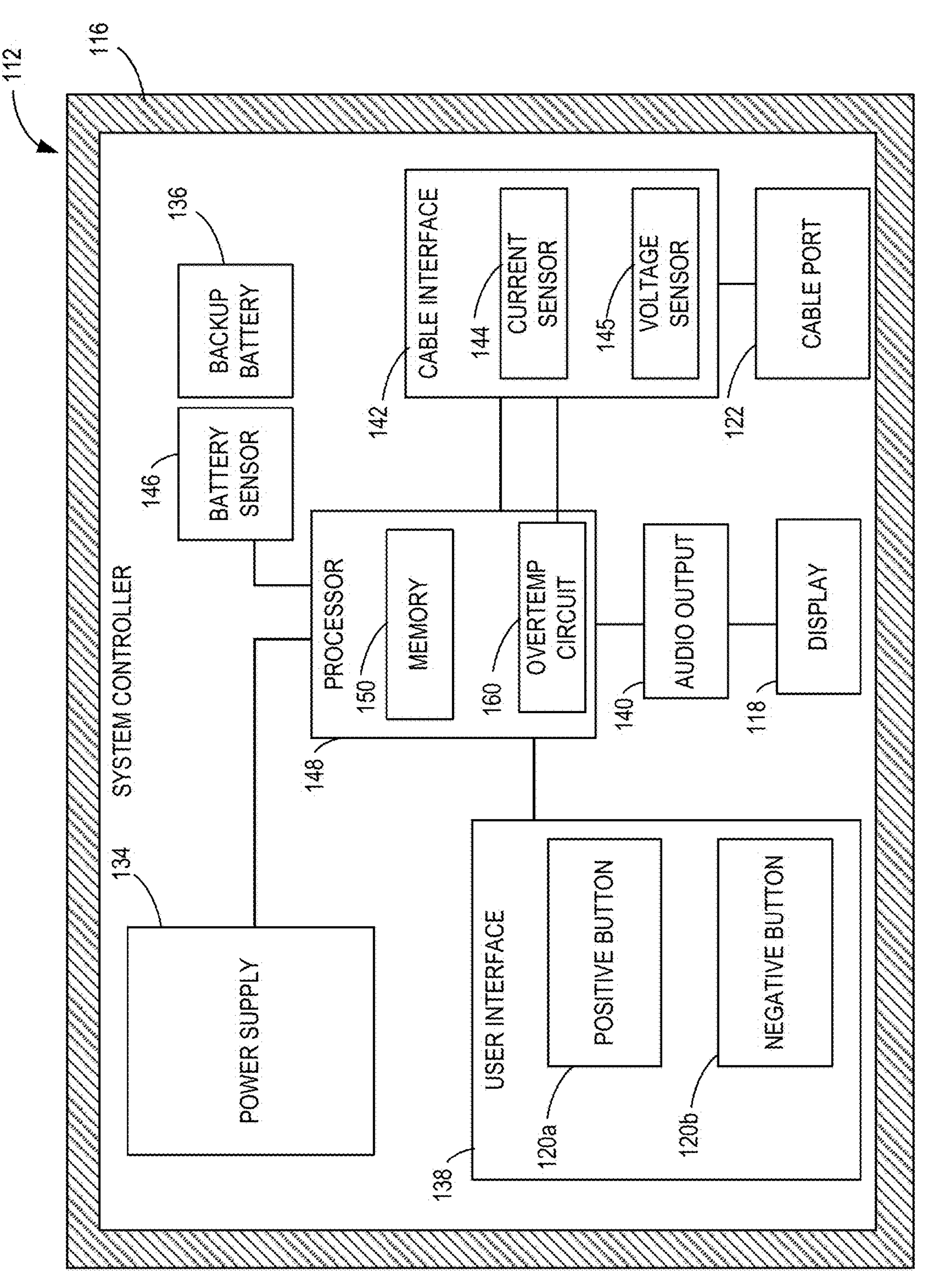
FIG. 5D is a schematic drawing of electrical components of a controller of a patient warming system, according to an example of the present disclosure.

As previously described, the patient support device 10 is configured to be used with a patient warming system 110 (shown in FIGS. 1A and 1B) including the controller 112 for providing electric current to the heating element 20 of the patient support device 10. FIGS. 5A-5C are drawings showing external features of the controller 112 of the patient warming system 110. FIG. 5D is a schematic drawing showing electrical components of the controller 112.

a. Warming System Controller

As shown in FIGS. 5A-5C, the controller 112 is contained within a device housing 116. The device housing 116 can be a rigid enclosure containing electrical components of the controller 112. In examples, the device housing 116 can comprise a substantially flat bottom so that the controller 112 can be placed on a flat surface, such as a table or shelf, and remain in an upright position. Alternatively or in addition, as described in further detail herein, the device housing 116 can comprise clips, clamps, hooks, or other connectors for securing the device housing 116 to and/or hanging the device housing 116 from poles, furniture, and other items in a surgical suite and near to the operating table 102.

As shown in FIG. 5A, the controller 112 comprises a visual display 118 connected to and/or enclosed by the housing 116 for displaying, for example, a selected or setpoint temperature for the patient support device 10 (e.g., a selected temperature of between 36° C. and 40° C.). The visual display 118 can also display, for example, a device start-up screen, a warming icon indicating when electric current is being applied to the patient support device 10 to warm the patient support device 10, and alarms or alerts indicating when the controller 112 and/or patient support device 10 are not operating in an expected manner. In examples, the housing 116 can further comprise user inputs, such as temperature selection button(s) 120*a*, 120*b* for increasing or decreasing the selected setpoint temperature. Pressing the temperature selection buttons can increase (positive button 120*a*) or decrease (negative button 120*b*) the selected temperature by a predetermined step or amount, such as by 0.1° C., 0.25° C., 0.5° C., or another selected step amount.

As shown in FIGS. 5B and 5C, the rear side of the device housing 116 can include a cable outlet or port 122 configured to receive the cable 114 that connects the patient support device 10 to the controller 112. As previously described, the cable 114 is configured to provide temperature sensor signals from the patient support device 10 to the controller 112 and to provide the electric current from the controller 112 to the patient support device 10. In examples, as shown in FIG. 5C, the outlet or port 122 can comprise multiple receptacles configured to receive corresponding prongs of the cable 114 for providing the electrical connection between the cable 114 and the controller 112. In examples, the outlet or port 122 can also comprise locking features, such as protrusions, ribs, or ridges, for providing a robust but removable connection between the cable 114 and port 122. The controller 112 can also include a power button or on/off switch 124 (shown in FIG. 5B) and plug 126 on the rear of the housing 116 for connecting the controller 112 to external power.

Figure 6A:
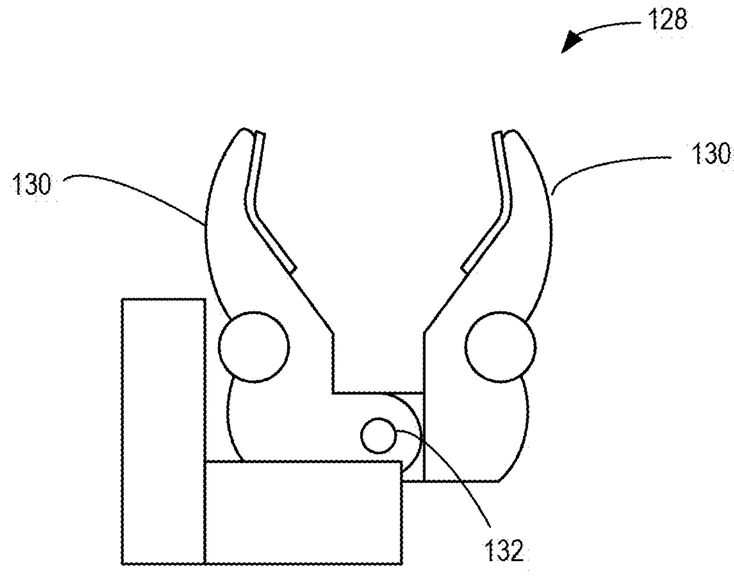
FIG. 6A is a top view of a clip configured to be attached to a rear surface of the controller of FIG. 5A, according to an example of the present disclosure.
Figure 6B:
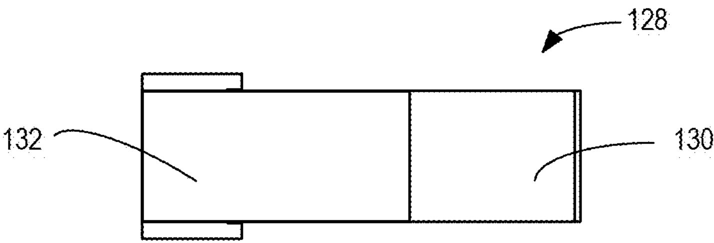
FIG. 6B is a side view of the clip of FIG. 6A.

In examples, the controller 112 can also comprise a mounting clamp or clip 128 attached to and extending from the rear surface of the housing 116. The clip 128 can be configured to mount the controller 112 onto an elongated member or pole 104, such as the IV pole shown in FIGS. 1A and 1B. FIGS. 6A and 6B are drawings showing enlarged views of the clip 128 in an open configuration. As shown in FIGS. 6A and 6B, the clip 128 comprises opposing arms 130, such as a first arm and a second arm, connected together at a pivot point 132 proximate to a rear surface of the clip 128. As shown in FIG. 5B, the rear surface of the clip 128 is secured to the housing 116 of the controller 112. The arms 130 are configured to grasp and press against the rod or pole 104 with a friction fit, thereby securing the controller 112 in place on the rod or pole 104. Desirably, the pole 104 can be moved to an inconspicuous location in the operating room, where the setpoint temperature shown on the visual display 118 is visible to caregivers, particularly to an anesthesiologist who may need to monitor patient temperature, but where the pole 104, controller 112, and cable 114 do not distract caregivers or obstruct them from performing assigned tasks.

b. Electrical Components of Warming System Controller

FIG. 5D is a schematic drawing of electrical components of the controller 112. As shown in FIG. 5D, the controller 112 comprises a power supply 134 for providing the electric current to the patient support device 10. The controller 112 can further comprise a backup battery 136, such as a low voltage coin-sized battery or similar disposable or rechargeable battery, for supplying electric power to the controller 112 when external power is not available. In particular, the backup battery 136 can be configured to provide functionalities including powering a battery-operated, real-time clock of the controller 112 and maintaining battery persisted storage when primary external power is removed from the controller 112. In examples, the real-time clock is used to measure a power-off duration of the controller 112 by, for example, subtracting a current timestamp (from the real time clock) at power-on from a last timestamp from the controller 112 prior to power-off. If the power-off duration is short (e.g., less than about 10 minutes), the controller 112 can be configured to maintain previous settings (e.g., to maintain the setpoint temperature from before power-off) at start-up of the controller 112. However, if the power-off duration is a longer period of time (e.g., longer than 10 minutes), the controller 112 can be configured to start-up using default settings. In examples, the controller 112 can further comprise a battery voltage sensor 146 configured to detect voltage of the backup battery 136. As described in further detail herein, the controller 112 can be configured to provide an alarm or alert when voltage measured by the battery voltage sensor 146 is below an expected or minimum threshold value.

In examples, the controller 112 further comprises a user interface 138 configured to receive inputs from a device user and, in particular to receive a setpoint temperature value entered by the user. In examples, as previously described, the user interface 138 can comprise the positive and negative temperature buttons 120*a*, 120*b* for increasing and decreasing the setpoint temperature. The controller 112 can also comprise outputs such as the visual display 118 that displays the setpoint temperature, as well as an audio outputs 140, as such speakers or buzzers, for providing audible alarms and alerts.

The controller 112 can further comprise a cable interface 142 configured to receive signals from the temperature sensors 32, 38 of the patient support device 10 and to provide the electric current from the power supply 134 to the heating element 20 of the patient support device 10. The cable interface 142 can be electrically connected to the cable port 122 or receptacle on the controller housing 116. In examples, the cable interface 142 can comprise circuitry for receiving and processing the signals received from the temperature sensors 32, 38. For example, the cable interface 142 can be configured to process received signals from actual temperature sensors 32 to convert resistance measurements to temperature values. In examples, the cable interface 142 can also comprise overtemperature circuitry for controlling the power supply 134 when an overtemperature error occurs indicating that temperature of the patient support device 10 exceeds the maximum permitted temperature (e.g., 42° C.). The cable interface 142 can also comprise circuitry, such as a current sensor 144 and/or voltage sensor 145, for monitoring the electric current and voltage being provided from the power supply 134 to the system cable 114. As described in further detail herein, the controller 112 can be configured to provide an alert or alarm when the applied current or voltage is outside of an expected or suitable range.

The controller 112 further comprises one or more computer processors 148 and associated computer-readable memory 150 for controlling operation of the controller 112. The processors 148 and memory 150 can be configured to monitor and control device functions including controlling heat being generated by the patient support device 10, monitoring current and voltage of the patient support device 10 and components of the controller 112, analyzing resistance signals received from the temperature sensor(s) 32 to determine temperature of the patient support device 10, and generating alarms and alerts when the controller 112 and/or patient support device 10 are not operating in an expected manner. In examples, the processors 148 and memory 150 can also be configured to implement start-up and self-test processes to confirm that the controller 112 is operating in an expected manner before applying the electric current to the patient support device 10.

More particularly, in examples, the processors 148 and memory 150 of the controller 112 can be configured to determine a temperature of the patient support device 10 based on resistance signals received from temperature sensors 32 of the patient support device 10. The processors 148 and memory 150 can also be configured to activate and deactivate the power supply 134 in order to control when the electric current is provided to the patient support device 10 based, at least in part, on the temperature signals received from the temperature sensors 32. The processors 148 and memory 150 can also be configured to monitor sensor and electrical signals received from the patient support device 10 to determine when the patient support device 10 is not operating in an expected manner. In examples, the processors 148 and memory 150 can also be configured to provide visual and audio alerts through audio outputs 140 when the controller 112 or patient support device 10 are not operating in the expected manner.

In examples, the process for controlling temperature of the patient support device 10 can include the following steps. First, the processors 148 can be configured to receive and process temperature information from the temperature senor 32 of the heating element 20 to determine a temperature of the patient support device 10. As previously described, measured resistance can be correlated with temperature with high resistance indicating low temperature. Once the temperature of the patient support device 10 is determined, the processors 148 can be configured to compare the determined temperature to the setpoint temperature value entered by the user. Based on the comparison, the processors 148 can also be configured to pause or cease warming of the patient support device 10 by, for example, causing the power supply 134 to cease applying the electric current to the heating element 20 when the determined temperature exceeds the setpoint temperature.

In examples, the comparison between the determined temperature value and the setpoint temperature value can be performed according to a two stage comparison algorithm. For example, the processors 148 and memory 150 can be configured to reduce the electric current applied to the heating element 20 linearly (e.g., by a predetermined amount per second) until the measured temperature of the patient support device 10 is within two degrees of the setpoint temperature value. For example, when the setpoint temperature is 38° C., the processors 148 can be configured to increase the electric current linearly (e.g., by about 0.1 amp/second) until the measured temperature reaches 36° C. When the measured temperature of the patient support device 10 is within two degrees of the setpoint temperature, the controller 112 can be configured to adjust the electric current according to a proportional-integral-derivative (PID) algorithm to obtain more accurate and precise temperature control.

In examples, the processors 148 and memory 150 of the controller 112 and/or the cable interface 142 can further comprise the overtemperature circuit 160. The overtemperature circuit 160 can be separate from and/or operate independently of the temperature control circuit that compares the measured temperature of the patient support device 10 to the setpoint temperature value. The overtemperature circuit 160 can be a failsafe separate independent circuit that causes the power supply 134 to cease applying electric current to the patient support device 10 when the temperature detected by the overtemperature sensor 38 exceeds, for example, the maximum permitted temperature of 42° C. The overtemperature circuit 160 is configured to receive a signal from the overtemperature sensor 38 of the heating element 20 when the temperature exceeds the predetermined expected or acceptable value, such as a value of 42° C. When the signal is received from the overtemperature circuit 160, the processors 148 can be configured to cause the power supply 134 to cease applying the electric current to the patient support device 10, which can prevent damage to the patient support device 10 and/or can prevent the patient from being exposed to temperatures above the maximum permitted temperature.

c. Controller Startup Processes and Self Tests

Figure 7:
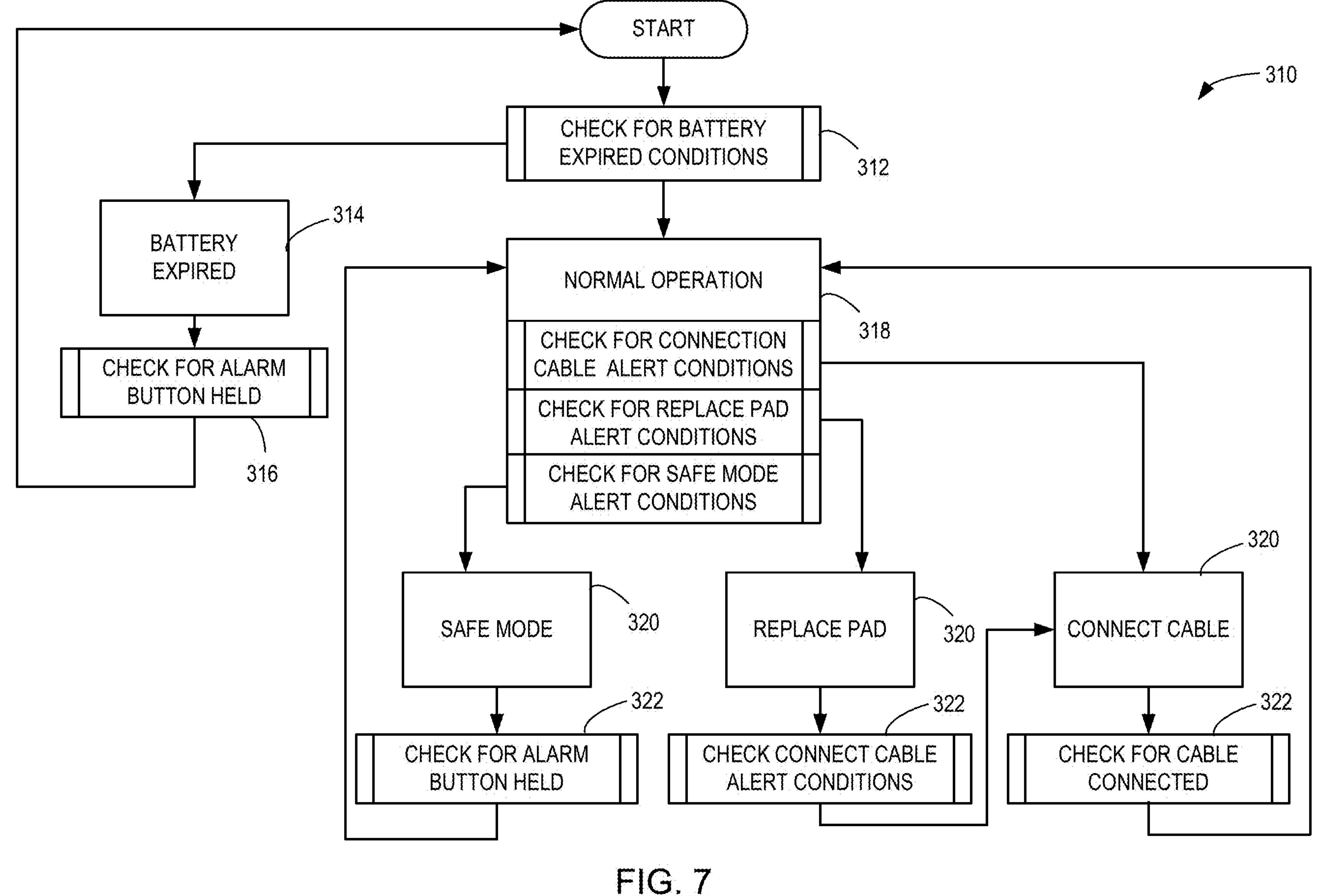
FIG. 7 is a flow chart of a startup process of a controller of a patient warming system, according to an example of the present disclosure.

In examples, the processors 148 and memory 150 of the controller 112 can also be configured to implement a startup process including one or more device self-tests to confirm that the controller 112 is operating correctly upon device startup. FIG. 7 is a flow chart showing an example startup process 310 that can be performed by the controller 112. As shown in FIG. 7, the startup process includes self-tests, such as a battery expired check, a cable check, and a patient support device or pad replacement check. The controller 112 can also be configured to operate in a "Safe Mode" when certain conditions are present.

More particularly, as shown in FIG. 7, the processor 148 first checks to determine whether the backup battery 136 has expired (at box 312). If the backup battery 136 has expired, a notification stating "Battery Expired" can be provided (box 314), which may remain in place until the user acknowledges the notification by, for example, pressing an alarm button of the user interface (box 316). After confirming that the backup battery 136 is not expired, at box 318, the processors 148 can be configured to initiate additional self-checks, specifically checking whether the cable 114 is connected, whether the pad needs to be replaced, and whether the controller 112 should operate in safe mode. If any of the checks fail, notifications can be provided to the user as shown at boxes 320. As with the battery expired notification, the notifications for the cable check, replace pad check, and safe mode can remain in place until the user presses the alar, button (322) to acknowledge the notification or alarm. Additional details about self-check actions performed by the processor 148 (at block 318 of FIG. 7) will now be described. Display screens showing examples of notifications that can be provided to the device user in response to the self-checks are shown in FIGS. 8A-8E.

Figure 8A:
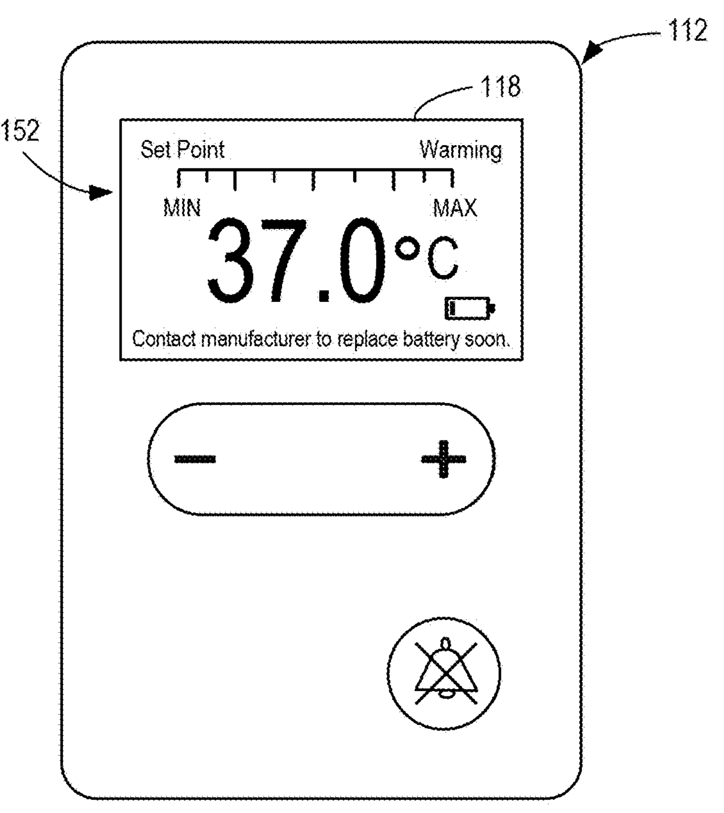
FIGS. 8A-8E are screen captures shown on a visual display of the controller notifying a user of different alerts and alarms, according to examples of the present disclosure.
Figure 8B:
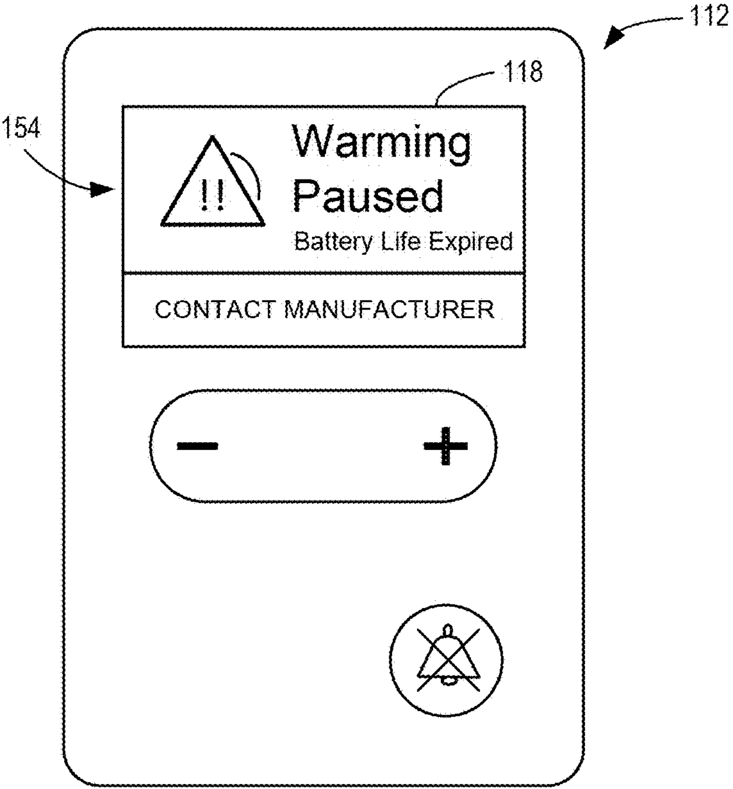
Figure 8C:
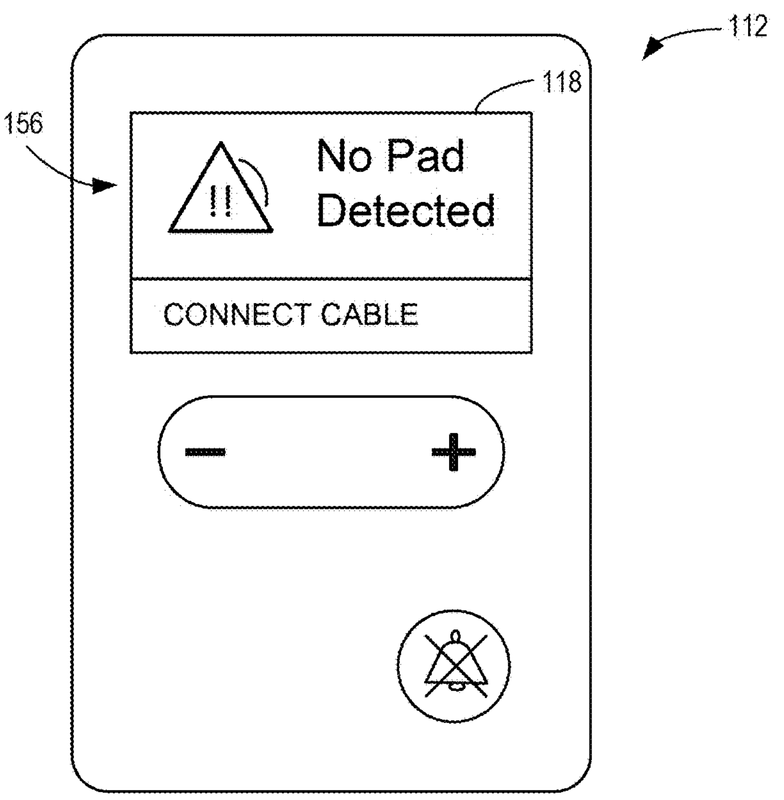

As previously described, the backup battery 136 is configured to provide power for the real-time clock and system memory 150 when external power is not available. The battery check is performed to ensure that the backup battery 136 voltage is sufficient and that the battery 136 is not expired. The battery check can comprise comparing a voltage of the battery 146 detected by the voltage sensor 146 to a predetermined threshold minimum voltage. For example, a measured voltage below a minimum voltage of 2.8 volts may indicate that the battery 136 has low voltage, is nearly depleted, and should be recharged or replaced. A measured voltage of below 2.0 volts may indicate that the battery is expired. If the battery check determines that the battery is low voltage or expired, the processors 148 can be configured to cause the visual display 118 to show a notification about the battery status. For example, as shown in FIG. 8A, a battery warning screen 152 is shown instructing the user that a low battery has been detected and that the user should contact the manufacturer for a replacement battery. As shown in FIG. 8B, when the detected voltage is below the battery expired value, a battery expired screen 154 can be displayed instructing the user to contact the manufacturer immediately to obtain a replacement battery. The processors 148 can also cause the audio output 140 to provide an audible alert (e.g., a bell, buzzer, or another conspicuous sound) instructing the user to review the information on the visual display 118 when the battery check is triggered.

The cable check is performed to ensure that the cable 114 connecting the patient support device 10 to the controller 112 is connected correctly and operating in an expected manner. In examples, the cable check can be configured to confirm that signals are received from all temperature sensors 32, 38 of the patient support device 10 and that the overtemperature circuit is not providing an error. More particularly, in examples, the processors 148 of the controller 112 can be configured to generate the cable check alert when: (i) all temperature sensors 32 of the heating element 20 have an open circuit with a resistance substantially exceeding expected values and (ii) the overtemperature circuit indicates an error meaning that a signal is not being received from the overtemperature sensor 38. In specific examples, the cable check alert can be generated when all of the temperature sensors 32 have open circuits meaning that the resistance of the circuits is greater than a predetermined threshold of, for example, 135,200 ohms (which corresponds to a measured temperature of −30° C.) and the overtemperature circuit indicates an error because no signal is received from the overtemperature sensor 38. When a cable check alert is generated, the processors 148 can be configured to cause the visual display 118 to provide a "No Pad" notification screen 156 shown in FIG. 8C indicating that no pad (e.g., no patient support device 10) is detected and instructing the user to connect the cable 114 to the controller 112. The audio output 140 can also emit an audible alert instructing the user to review the information on the visual display 118.

Figure 8D:
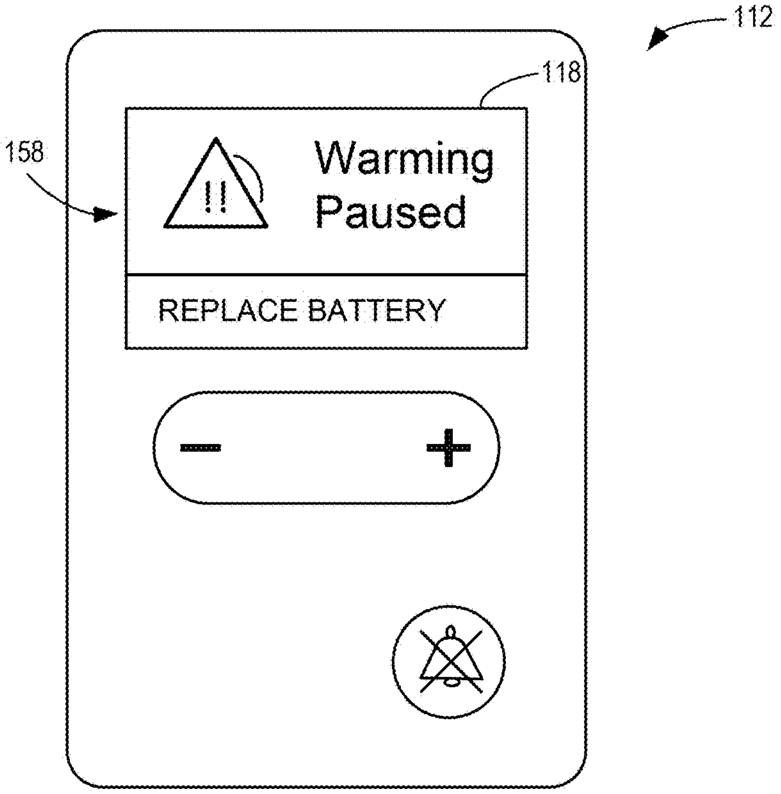
Figure 8E:
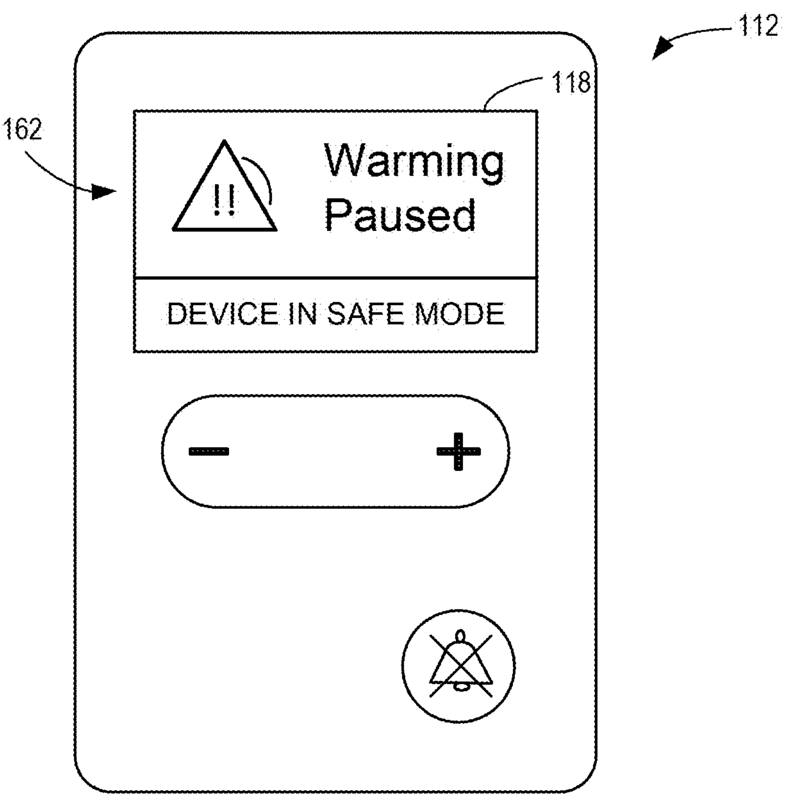

The check of whether the patient support device 10 should be replaced is performed to confirm that the patient support device 10 is capable of operating as expected manner and to warm to the setpoint temperature selected by the user. In examples, this check can provide a notification to replace the patient support device 10 when one or more of the following conditions occur: electric current of the patient support device 10 measured by the current sensor 144 of the controller 112 is outside of a predetermined acceptable range; the overtemperature circuit produces an error indicating that the maximum temperature is exceeded; any of the temperature sensors 32 measure a resistance substantially greater than an expected value; or any of the temperature sensors 32 register unexpectedly low resistance indicating a temperature substantially greater than a maximum expected or reasonable temperature (e.g., greater than 42° C.). In examples, a range of acceptable electric currents for the patient support device 10 may be between 0.2 A and 2.5 A. The patient support device 10 may need to be replaced if electric current detected by the current sensor 144 is outside of this acceptable range. As previously described, the maximum permitted temperature for the patient support device 10 may be 42° C. If the overtemperature circuit or any of the other temperature sensors 32, 38 detect a temperature greater than 42° C., the processors 148 can be configured to generate the replace pad alert. When the replace pad alert is generated, the one or more processors 148 can be configured to cause the power supply 134 to cease applying the electric current to the heating element 20 to pause warming. Also, the processors 148 can cause the visual display 118 to show a notification screen 158 stating that warming has been paused and instructing the user to replace the pad (e.g., the patient support device 10) as shown in FIG. 8D. The processors 148 can also be configured to cause the audio output 140 to emit an audible alert instructing the user to review the information shown in the visual display 118.

In examples, the processors 148 and memory 150 of the controller 112 can also be configured to enter a safe operation mode when certain unexpected conditions occur. In the safe mode, the processors 148 can cause the power supply 134 to cease applying electric current to the patient support device 10 and provide a notification to the user that the controller 112 has entered the safe mode. For example, the processors 148 can be configured to cause the controller 112 to enter the safe mode when any of the following conditions occur: the output voltage of the power supply 134, as measured by the voltage sensor 145, is outside of a predetermined range; output electric current to the patient support device 10 is outside of a predetermined range as measured by the current sensor 144; any of the temperature sensors 32 measure a resistance substantially less than or greater than an expected value, which would indicate either an open circuit or unsafe temperature; or temperatures detected by multiple temperature sensors 32 differ by more than about 5° C. indicating uneven heating. More particularly, in examples, the processors 148 of the controller 112 can be configured to enter the safe mode when output voltage of the power supply 134 as measured by the voltage sensor 145 is, for example, less than 44 volts or greater than 52 volts because voltages outside of the expect range would cause the heating element 20 to operate in an unintended manner. Also, the output electric current to the patient support device 10, as measured by the current sensor 144, should be within a range of, for example, 0.6 A to 2.4 A. The processors 148 can also be configured to enter the safe mode when the cable 114 is connected between the controller 112 and patient support device 10, but the overtemperature circuit is open, short circuited, or indicates that the patient support device 10 exceeds the maximum permitted temperature (e.g., 42° C.). Alternatively or in addition, the processors 148 may cause the controller 112 to enter the safe mode when the cable 114 is connected, but any of the temperature sensors 32 appear to have an open circuit, as indicated by an unexpectedly high measured resistance (e.g., 135,200 ohms which would indicate a temperature of −30° C.). In examples, the processors 148 can also be configured to cause the controller 112 to enter the safe mode when any of the temperature sensors 32 measure a temperature than exceeds the setpoint temperature by more than a predetermined amount, such as by more than 2° C., which may indicate that the heating element 20 is failing to heat correctly even when electric current is applied to the heating element 20.

When the controller 112 enters the safe mode, the processors 148 can be configured to cause the visual display 118 to show a notification screen 162 (shown in FIG. 6E) that warming has been paused and that the controller 112 is in safe mode. The audio output 140 may also issue an audible alert instructing the user to review the information shown on the visual display 118. In examples, the controller 112 may remain in safe mode until the condition which caused the controller 112 to enter safe mode is resolved or until, for example, the controller 112 is serviced and reset by a technician or another service provider. Once the controller 112 exits safe mode, the user can connect the patient support device 10 to the controller 112 with the cable 114 and can continue to use the controller 112 and patient support device 10 in the instructed manner.

While examples of the patient support device 10, patient warming system 110, and methods of use of the present disclosure are shown in the accompanying figures and described hereinabove in detail, other examples will be apparent to, and readily made by, those skilled in the art without departing from the scope and spirit of the invention. Accordingly, the foregoing description is intended to be illustrative rather than restrictive. The invention described hereinabove is defined by the appended claims, and all changes to the invention that fall within the meaning and the range of equivalency of the claims are to be embraced within their scope.

What is claimed is:

1. A heated patient support device for positioning a patient on an operating table during a surgical procedure, the patient support device comprising:

a foam body comprising a substantially flat first surface configured to be in contact with the patient, an opposing substantially flat second surface configured to contact the operating table for holding the patient support device in place against the operating table, and a peripheral edge extending therebetween; and at least one heating element at least partially enclosed within the foam body, the at least one heating element comprising:

a first insulation portion comprising a cloth sheet and an adhesive over an outwardly facing surface of the cloth sheet, a graphene layer on an inwardly facing surface of the cloth sheet configured to generate heat when electric current is applied to the graphene layer, a second insulation portion comprising another cloth sheet and adhesive over an outwardly facing surface of the another cloth sheet, a copper film between the first insulation portion and the second insulation portion, and a silver adhesive layer between the graphene layer and the copper film that adheres the copper film to the graphene layer and to the cloth sheet.

2. The support device of claim 1, wherein the foam body comprises an upper foam block comprising the first surface and a lower foam block comprising the second surface, and wherein the at least one heating element is positioned between the upper foam block and the lower foam block.

3. The support device of claim 2, wherein the upper foam block and the lower foam block comprise a same type of biodegradable and viscoelastic foam material.

4. The support device of claim 1, wherein portion(s) of the foam body configured to contact the operating table have a coefficient of friction sufficient to restrict the foam body from sliding over the operating table when the operating table is moved to an angle between 10 degrees and 45 degrees.

5. The support device of claim 1, wherein portion(s) of the foam body configured to be in contact with the patient are configured to form depressions within the foam body due to body weight of the patient, the depressions preventing the patient from sliding over the first surface of the foam body.

6. The support device of claim 1, wherein the at least one heating element further comprises a plurality of temperature sensors for measuring a temperature of the patient support device positioned over the graphene layer for measuring temperature proximate to the graphene layer.

7. The support device of claim 1, wherein the cloth sheet or the another cloth sheet comprises a woven or knitted cloth sheet.

8. The support device of claim 1, wherein the copper film of the at least one heating element comprises first and second copper film segments extending along opposing sides of the foam body, and wherein the graphene layer of the at least one heating element comprises a plurality of graphene segments extending between the first copper film segment and the second copper film segment.

9. The support device of claim 8, wherein the plurality of graphene segments are about 5 mm to 15 mm wide and spaced apart from adjacent graphene segments by at least about 5 mm.

10. The support device of claim 1, wherein the at least one heating element has an Ingress Protection (IPXX) rating for solid particle protection of from 1 to 6 and for liquid ingress protection of from 1 to 9.

11. A patient warming system, comprising:

the patient support device of claim 1, wherein the at least one heating element further comprises at least one temperature sensor for measuring a temperature of the patient support device proximate to the at least one heating element, and at least one controller configured to supply the electric current to the at least one heating element causing the at least one heating element to produce heat to warm the patient support device.

12. The patient warming system of claim 11, wherein the at least one controller is configured to receive and process temperature information from the at least one temperature senor; determine a temperature of the patient support device based on the received and processed information; compare the determined temperature to a setpoint temperature value; and cease applying the electric current to the at least one heating element when the determined temperature is equal to or exceeds the setpoint temperature value.

13. The patient warming system of claim 12, wherein, in response to the comparison between the determined temperature to the setpoint temperature value, the at least one controller is configured to reduce the electric current applied to the at least one heating element linearly until the determined temperature is within two degrees of the setpoint temperature value and then to adjust the electric current according to a proportional-integral-derivative (PID) algorithm when the measured temperature is within two degrees of the setpoint temperature value.

14. The patient warming system of claim 12, wherein the at least one heating element of the patient support device comprises multiple temperature sensors, and wherein the at least one controller is configured to cease applying the electric current to the at least one heating element when a maximum temperature measured by any of the multiple temperature sensors is above a predetermined threshold temperature value.

15. The patient warming system of claim 12, wherein the at least one heating element of the patient support device comprises multiple temperature sensors, and wherein the at least one controller is configured to cease applying electric current to the at least one heating element when temperatures detected by the multiple temperature sensors vary by more than about 5° C.

16. The patient warming system of claim 12, wherein the at least one controller is configured to initiate a controller self-test at start-up, the controller self-test comprising a battery check, cable check, and a patient support device check.

17. The patient warming system of claim 16, wherein the at least one controller is configured to perform the cable check and generate a cable check alert when the cable check identifies the following conditions:

all temperature sensors of the at least one heating element have an open circuit with a measured resistance substantially exceeding expected values; and a dedicated overtemperature monitoring circuit of the patient support device indicates an error.

18. The patient warming system of claim 16, wherein the at least one controller is configured to provide a notification to replace the patient support device when the patient support device check determines that one or more of the following conditions have occurred:

electric current of the patient support device measured by the at least one controller is outside of a predetermined acceptable range;

a dedicated overtemperature circuit error occurs;

any of the temperature sensors measure a resistance substantially greater than an expected value; or any of the temperature sensors measure resistance values indicating a temperature substantially greater than an acceptable maximum temperature.

19. A method of assembly for a heated patient support device, comprising:

assembling at least one heating element, the at least one heating element comprising a first insulation portion comprising a cloth sheet and an adhesive over an outwardly facing surface of the cloth sheet, a graphene layer on an inwardly facing surface of the cloth sheet configured to generate heat when an electric current is applied to the graphene layer, a second insulation portion comprising another cloth sheet and adhesive over an outwardly facing surface of the another cloth sheet, a copper film between the first insulation portion and the second insulation portion, and a silver adhesive layer between the graphene layer and the copper film that adheres the copper film to the graphene layer and to the cloth sheet;

removing a lower removable cover sheet from a lower surface of the at least one heating element exposing a lower adhesive layer;

attaching the at least one heating element to a lower foam block such that the lower adhesive layer adheres the at least one heating element to the lower foam block;

removing a removable upper cover sheet from an upper surface of the at least one heating element exposing an upper adhesive layer; and attaching the at least one heating element to an upper foam block such that the upper adhesive layer adheres the at least one heating element to the upper foam block, thereby enclosing the at least one heating element between the upper foam block and the lower foam block forming the heated patient support device.

* * * * *